(12) United States Patent
Struebing

(10) Patent No.: US 8,193,150 B2
(45) Date of Patent: Jun. 5, 2012

(54) IMPROVING VASCULAR FUNCTION WITH AN INACTIVATING MUTANT OF A TRPC CHANNEL PROTEIN

(75) Inventor: Carsten Struebing, Frankfurt (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/217,755

(22) Filed: Aug. 25, 2011

(65) Prior Publication Data

US 2011/0312874 A1      Dec. 22, 2011

Related U.S. Application Data

(60) Division of application No. 12/897,892, filed on Oct. 5, 2010, now Pat. No. 8,030,276, which is a continuation of application No. 11/813,542, filed as application No. PCT/EP2005/013977 on Dec. 23, 2005, now abandoned.

(30) Foreign Application Priority Data

Jan. 12, 2005   (EP) ................................ 05000440

(51) Int. Cl.
*A61K 38/00*      (2006.01)
*C07K 14/00*      (2006.01)

(52) U.S. Cl. .......................... 514/12; 530/350

(58) Field of Classification Search .......... None
See application file for complete search history.

(56) References Cited

U.S. PATENT DOCUMENTS

2005/0182011 A1    8/2005    Olson et al.

FOREIGN PATENT DOCUMENTS

| WO | WO 02/059155 A2 | 8/2002 |
| WO | WO 02/072824 | 9/2002 |
| WO | WO 2005/049084 A2 | 6/2005 |

OTHER PUBLICATIONS

Bergdahl, et al., Cholesterol depletion impairs vascular reactivity to endothelin-1 by reducing store-operated Ca2+ entry dependent on TRPC1, Circulation Research, vol. 93, No. 9, Oct. 31, 2003, pp. 839-847.
Zhu et al., Receptor activated Ca2+ Influx via Human Trp3 Stably Expressed in Human Embryonic Kidney (HEK)293 Cells, J. of Biol. Chem., vol. 273, No. 1, Jan. 2, 1998, pp. 133-142.
Groschner et al., Trip proteins form store-operated cation channels in human vascular endothelial cells, FEBS Letters, vol. 437, No. 1-2, Oct. 16, 1998, pp. 101-106.
Hofmann et al., Subunit composition of mammalian transient receptor potential channels in living cells, PNAS USA, vol. 99, No. 11, May 28, 2002, pp. 7461-7466.
Strubing et al., Formation of novel TRPC channels by complex subunit interactions in embryonic brain, J. of Biological Chemistry, vol. 278, No. 40, Oct. 3, 2003, pp. 39014-39019.
Vandebrouck et al., Involvement of TRPC in the abnormal calcium influx observed in dystrophic (mdx) mouse skeletal muscle fibers, J. of Cell Biology. vol. 158, No. 6, Sep. 16, 2002, pp. 1089-1096.
Yip et al., Expression of TRPC homologs in endothelial cells and smooth muscle layers of human arteries, Histochemistry and Cell Biology, vol. 122, No. 6, Dec. 2004, pp. 553-561.
Golovina et al., Upregulated TRP and enhanced capacitative Ca2+ entry in human pulmonary artery myocytes during proliferation, Am J. Physiol Heart Circ Physiol, vol. 280, 2001, pp. H746-H755.
International Search Report for WO2006/074802 dated Jul. 20, 2006.

*Primary Examiner* — Ruixiang Li

(57) ABSTRACT

The invention refers to the use of a TRPC channel, an inactivating mutant thereof, or a nucleotide sequence coding for the TRPC channel or for the inactivating mutant for the production of a medicament for the treatment of a cardiovascular disease and a method of screening a modulator of the TRPC channel or an inactivating mutant thereof.

1 Claim, 8 Drawing Sheets

IMPROVING VASCULAR FUNCTION WITH AN INACTIVATING MUTANT OF A TRPC CHANNEL PROTEIN

The invention refers to the use of a TRPC channel, an inactivating mutant thereof, or a nucleotide sequence coding for the TRPC channel or for the inactivating mutant for the production of a medicament for the treatment of a cardiovascular disease and a method of screening a modulator of the TRPC channel or an inactivating mutant thereof.

Atherosclerosis is one of the major causes of cardiovascular diseases in the Western world. In 2001 these diseases accounted for about 1 million deaths in the USA. Moreover, due to live style changes in the developing countries atherosclerosis and related cardiovascular diseases are becoming global epidemics. The WHO reports that cardiovascular diseases will be the leading cause of death in the developing world by 2010.

Thus, there is an immense medical need for new medicines that prevent and treat atherosclerosis. The generation and progression of atherosclerosis is a complex and incompletely understood process that is dependent on a number of epigenetic (e.g. life style, nutrition, exercise) and genetic factors. Numerous clinical observations implicate dysfunction of endothelial cells that line the inner vessel wall in the pathophysiology of atherosclerosis and atherogenesis (Ross, R. N. (1999), Engl. J. Med. 340:115-126).

Therefore, proteins involved in the regulation of endothelial function might be primary targets for anti-atherosclerotic therapies. $Ca^{2+}$-regulatory proteins seem to be of particular interest as important endothelial functions such as the production of nitric oxide (NO) are controlled by the level of intracellular $Ca^{2+}$.

TRPC channels, a novel class of ion channel proteins, are $Ca^{2+}$ permeable non-selective cation channels expressed in the cardiovascular and other systems. Based on sequence homology TRPC3, TRPC6 and TRPC7 constitute a distinct TRPC subfamily. In expression systems these channels are activated by G protein coupled receptors or depletion of intracellular $Ca^{2+}$ stores (Clapham et al. (2001), Nat. Rev. Neurosci. 2:387-396). TRPC3 might also contribute to oxidative stress-activated cation currents in cultured endothelial cells (Balzer et al. (1999) Cardiovasc. Res. 42:543-549).

In order to study the functional role of TRPC1 in smooth muscle cells an antibody against a specific epitope of TRPC1 was used in WO 02/059155. However, this epitope is not found on other TRPC channels. WO 05/049084 discloses functional studies on isolated rat ventricular myocytes using the compound 2-aminoethoxydiphenylborate (2-APB). However, it is known that this compound shows unspecific and questionable effects in particular on TRPC3 (van Rossum et al. (2000), J. Biol. Chem., 275, 28562-28568).

According to the present invention we have suppressed TRPC3, TRPC6 and TRPC7 activity in endothelial cells of atherosclerotic rabbits in vivo using a genetic approach. Surprisingly, we found a dramatic improvement of vascular function and reduction of histological markers of atherosclerosis in vessels treated with a dominant negative TRPC3 gene, which means that the suppression of the activity of TRPC channels, in particular of the channels mentioned above, shows an anti-atherosclerotic effect. These findings establish a novel link between TRPC channels and cardiovascular diseases as atherosclerosis.

Therefore, one subject matter of the present invention is directed to the use of a TRPC channel, an inactivating mutant thereof, or a nucleotide sequence coding for the TRPC channel or for the inactivating mutant for the production of a medicament for the treatment of a cardiovascular disease, in particular atherosclerosis.

Preferred TRPC channels are the TRPC3 channel, TRPC6 channel or TRPC7 channel, in particular the TRPC3 channel or TRPC6 channel, especially the TRPC3 channel.

The corresponding amino acid sequences are SEQ ID NO: 1 (TRPC3), SEQ ID NO: 5 (TRPC6), and SEQ ID NO: 9 (TRPC7), in particular the amino acid sequence SEQ ID NO: 1 coding for the TRPC3 channel. The corresponding nucleotide sequences are SEQ ID NO: 2 (TRPC3), SEQ ID NO: 6 (TRPC6), and SEQ ID NO: 10 (TRPC7), in particular the nucleotide sequence SEQ ID NO: 2 coding for the TRPC3 channel.

According to the present invention the term "inactivating mutant" means a mutant which is functionally inactive as a cation channel but can suppress the channel activity of homologous naturally occurring TRPC channels. Suppression may be accomplished by replacing a homologous TRPC channel subunit in the native multimeric channel assembly with the effect that essentially all naturally occurring TRPC channels in the cell membrane contain mutant channel subunits or are totally replaced by the mutant channel. Mutations that render a channel subunit inactive may be preferably located within the pore regions of TRPC3 (amino acids 603-645 in SEQ ID NO: 1), TRPC6 (amino acids 660-705 in SEQ ID NO: 5) and TRPC7 (amino acids 610-650 in SEQ ID NO: 9). Particular examples are the mutant TRPC3 channel (TRPC3$^{DN}$) with the amino acid sequence of SEQ ID NO: 3, the mutant TRPC6 channel (TRPC6$^{DN}$) with the amino acid sequence of SEQ ID NO: 7, and the mutant TRPC7 channel (TRPC7$^{DN}$) with the amino acid sequence of SEQ ID NO: 11. A nucleotide sequence coding for TRPC3$^{DN}$ is the nucleotide sequence of SEQ ID NO: 4; a nucleotide sequence coding for TRPC6$^{DN}$ is the nucleotide sequence of SEQ ID NO: 8, and a nucleotide sequence coding for TRPC7$^{DN}$ is the nucleotide sequence of SEQ ID NO: 12. A particularly preferred example is the dominant-negative mutant TRPC3$^{DN}$ with the amino acid sequence of SEQ ID NO: 3. A nucleotide sequence coding for TRPC3$^{DN}$ is the nucleotide sequence of SEQ ID NO: 4.

Moreover, "inactivating mutants" may consist of any part of TRPC3, TRPC6 or TRPC7 that retain the ability to interact with naturally occurring TRPC channels at any step of protein synthesis or transport to the plasmamembrane and thereby suppress the function of the naturally occurring TRPC channels. Such part may be for example amino acids 0-302 of TRPC3 (SEQ ID NO: 1) (see Balzer et al. (1999) Cardiovasc. Res. 42:543-549).

Inactivating mutants may be detected and/or analyzed using the whole cell patch clamp method as exemplarily described in the Examples.

Another subject matter of the present invention is directed to the use of a TRPC channel, an inactivating mutant thereof, or a nucleotide sequence coding for the TRPC channel or for the inactivating mutant for the discovery of a TRPC channel modulator, in particular an inhibitor, as a medicament for the treatment of a cardiovascular disease, in particular atherosclerosis.

Preferred TRPC channels are the TRPC3 channel, TRPC6 channel or TRPC7 channel, in particular the TRPC3 channel or TRPC6 channel, especially the TRPC3 channel, as described above in detail.

In general, the TRPC channel or an inactivating mutant thereof, or a nucleotide sequence coding for the TRPC channel or for the inactivating mutant thereof is brought into contact with a test compound and the influence of the test compound on the TRPC channel, an inactivating mutant thereof, or a nucleotide sequence coding for the TRPC channel or for the inactivating mutant is measured or detected.

According to the present invention the term "TRPC channel modulator" means a modulating molecule ("modulator") of the TRPC channel, in particular an inhibitory or activating molecule ("inhibitor" or "activator"), especially an inhibitor of the TRPC channel identifiable according to the assay of the present invention. An inhibitors is generally a compound that, e.g. bind to, partially or totally block activity, decrease, prevent, delay activation, inactivate, desensitize, or down-regulate the activity or expression of at least one of the TRPC channels as preferably described above in detail. An activator is generally a compound that, e.g. increase, open, activate, facilitate, enhance activation, sensitize, agonize, or up-regulate the activity or expression of at least one of the TRPC channels as preferably described above in detail. Such modulators include genetically modified versions of the TRPC channels, preferably an inactivating mutant of the TRPC channels, such as TRPC3$^{DM}$, as well as naturally occurring or synthetic ligands, antagonists, agonists, peptides, cyclic peptides, nucleic acids, antibodies, antisense molecules, ribozymes, small organic molecules and the like.

An example for the measurement of the TRPC channel activity is an assay comprising the steps of:
(a) contacting a fluorescent cell expressing a TRPC channel,
(b) stimulating $Ca^{2+}$ influx by a channel activator before, simultaneously or after contacting the fluorescent cell with the modulator or test compound, and
(c) measuring or detecting a change in fluorescence.

Further details and alternative or preferred embodiments of that assay are described below and in the Examples.

Therefore, another subject matter of the present invention is directed to a method of screening a modulator of TRPC or an inactivating mutant thereof, or a nucleotide sequence coding for TRPC or for the inactivating mutant, wherein the method comprises the steps of:
(a) contacting a cell expressing a TRPC channel or an inactivating mutant thereof,
(b) stimulating $Ca^{2+}$ influx by a channel activator before, simultaneously or after contacting the cell with a test compound, and
(c) measuring or detecting a change of the TRPC channel activity.

In a preferred embodiment the method further comprises the step of:
(d) selecting a test compound with an activity against a cardiovascular disease by comparing the changes of the TRPC channel activity in the absence of the test compound.

In another preferred embodiment the expression of the TRPC channel or an inactivating mutant thereof in the cell is controlled by an inducible promoter, preferably by a promoter which is selected from a tetracycline inducible promoter.

In a particular preferred embodiment the cell is a fluorescent cell as e.g. further described below.

Preferred cells or cell lines according to the present invention are MDCK, HEK 293, HEK 293 T, BHK, COS, NIH3T3, Swiss3T3 or CHO cells, in particular a HEK 293 cell line.

TRPC channel activity can be measured or detected by measuring or detecting a change in ion fluxes, in particular $Ca^{2+}$ fluxes, by e.g. patch clamp techniques, whole cell currents, radiolabeled ion fluxes, or in particular fluorescence e.g. using voltage-sensitive dyes or ion-sensitive dyes (Vestergarrd-Bogind et al. (1988), J. Membrane Biol., 88:67-75; Daniel et al. (1991) J. Pharmacol. Meth. 25:185-193; Hoevinsky et al. (1994) J. Membrane Biol., 137:59-70; Ackerman et al. (1997), New Engl. J. Med., 336:1575-1595; Hamil et al. (1981), Pflugers. Archiv., 391:185).

Examples of such dyes are Di-4-ANEPPS (pyridinium 4-(2(6-(dibutylamino)-2-naphthalenyl)ethenyl)-1-(3-sulfopropyl) hydroxide), CC-2-DMPE (1,2-ditetradecanoyl-sn-glycero-3-phosphoethanolamine triethylammonium), DiSBAC2 (bis-(1,2-dibarbituric acid)-trimethine oxanol), DisBAC3 ((bis-(1,3-dibarbituric acid)-trimethine oxanol), SBFI-AM (1,3-benzenedicarboxylic acid,4,4'-[1,4,10-trioxa-7,13-diazacyclopentadecane-7,13-diylbis(5-methoxy-6, 12-benzofurandiyl)]bis-(tetrakis-[(acetyloxy)methyl]ester)), fluo3am(1-[2-Amino-5-(2,7-dichloro-6-hydroxy-3-oxy-9-xanthenyl)phenoxy]-2-(2'-amino-5'-methylphenoxy)ethane-N,N,N',N'-tetraacetic), fluo4am(1-[2-Amino-5-(2,7-dichloro-6-hydroxy-4-oxy-9-xanthenyl)phenoxy]-2-(2'-amino-5'-methylphenoxy)ethane-N,N,N',N'-tetraacetic) or fura2am(1-[2-(5'-carboxyoxazol-2'-yl)-6-aminobenzofuran-5-oxy]-2-(2'-amino-5'-methyl-phenoxy)-ethane-N,N,N',N'-tetraacetic).

Examples of the channel activators are diacylglycerols, in particular 1-Oleyl-2acetyl-sn-glycerol (OAG), $G_q$-coupled receptor agonists, such as phenylephrine and in particular trypsin, an agonist that stimulates receptor tyrosine kinases such as epidermal growth factor (EGF) or diacylglycerol generating enzymes such as phospholipases or activators thereof.

The channel activators, in particular OAG, can be used for the direct stimulation of the TRPC channels which is an additional advantage of the assay of the present invention compared to the indirect, receptor-mediated activation of the channels because, for example, in the present assay the rate of false-positive results are substantially reduced.

In general, a cell is provided which expresses a TRPC channel or an inactivating mutant thereof under an inducible promoter, as e.g. described above. Such cell can be produced using genetic methods known to a person skilled in the art and as described in the Examples. After having induced the expression of the TRPC channel or an inactivating mutant thereof the cells are usually plated into e.g. microtiter plates and grown. Usually the cells grow at the bottom of multiwell plates and are fixed. Thereafter, the cells are generally washed and loaded with a dye in a suitable loading buffer, preferably with a fluorescent dye such as fluo4am. After having removed the loading buffer, the cells are incubated with the test compound or modulator, in particular with a biochemical or chemical test compound as described above, e.g. in the form of a chemical compound library. $Ca^{2+}$ measurements can be carried out using e.g. a Fluoresense Imaging Plate Reader (FLIPR). To stimulate $Ca^{2+}$ influx through the TRPC channel a channel activator such as OAG should generally be applied.

As an alternative mode of TRPC channel activation trypsin as a $G_q$-coupled receptor agonist can be applied.

The expected effects of inhibitors would be a reduction of e.g. the fluorescence increase. Activators would lead to a further increase of e.g. an activator-evoked fluorescence or induce e.g. an activator-independent fluorescence increase.

Thereafter, suitable modulators, in particular inhibitors can be analyzed and/or isolated. For the screening of chemical compound libraries, the use of high-throughput assays are preferred which are known to the skilled person or which are commercially available.

According to the present invention the term "chemical compound library" means a plurality of chemical compounds that have been assembled from any of multiple sources, including chemically synthesized molecules and natural products or combinatorial chemical libraries.

Advantageously the method of the present invention is carried out on an array and/or in a robotics system e.g. including robotic plating and a robotic liquid transfer system, e.g. using microfluidics, i.e. channelled structured.

In another embodiment of the present invention, the method is carried out in form of a high-through put screening system. In such a system advantageously the screening method is automated and miniaturized, in particular it uses miniaturized wells and microfluidics controlled by a roboter.

In a particularly preferred embodiment the assay/method of the present invention is carried out in a cell line containing a gene of a TRPC channel under the control of an inducible promoter, as detailed above, wherein the channel activator is solubilised. For example, preferably the activator OAG is solubilised in the presence of a serum albumin, e.g. bovine serum albumin, or plutonic acid.

Another subject matter of the present invention is directed to a method for producing a medicament for the treatment of atherosclerosis, wherein the method comprises the steps of:
(a) carrying out the method as described above,
(b) isolating a detected test compound suitable for the treatment of a cardiovascular disease, in particular atherosclerosis, and
(c) formulating the detected test compound with one or more pharmaceutically acceptable carriers or auxiliary substances.

Pharmaceutically acceptable carriers or auxiliary substances are for example a physiological buffer solution, e.g. sodium chloride solution, demineralised water, stabilizers, such as protease or nuclease inhibitors, or sequestering agents, such as EDTA.

The following Figures, Sequences and Examples shall explain the present invention without limiting the scope of the invention.

DESCRIPTION OF THE SEQUENCES

Figure 1A:
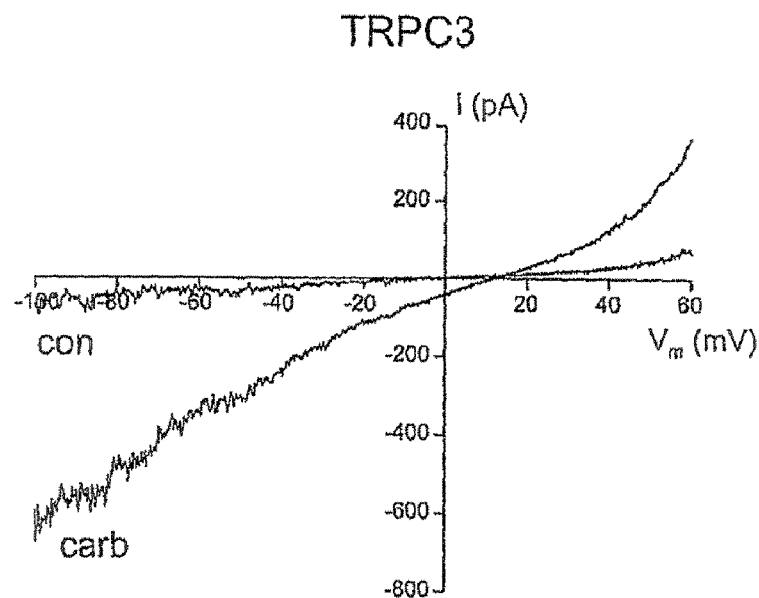
FIGS. 1A and 1B show that TRPC3$^{DN}$ does not carry functional ion currents

SEQ ID NO: 1 shows the amino acid sequence of TRPC3
SEQ ID NO: 2 shows a nucleotide sequence coding for TRPC3
SEQ ID NO: 3 shows the complete amino acid sequence of the dominant-negative
TRPC3 channel (TRPC3$^{DN}$), (mutated amino acids are in bold)
SEQ ID NO: 4 shows the complete nucleotide sequence of TRPC3$^{DN}$; (mutated nucleotides are in bold)
SEQ ID NO: 5 shows the amino acid sequence of TRPC6
SEQ ID NO: 6 shows a nucleotide sequence coding for TRPC6
SEQ ID NO: 7 shows the amino acid sequence of a dominant-negative TRPC6 channel (TRPC6$^{DN}$), (mutated amino acids are in bold)
SEQ ID NO: 8 shows the complete nucleotide sequence of TRPC6$^{DN}$; (mutated nucleotides are in bold)
SEQ ID NO: 9 shows the amino acid sequence of TRPC7
SEQ ID NO: 10 shows a nucleotide sequence coding for TRPC7
SEQ ID NO: 11 shows the amino acid sequence of a dominant-negative TRPC7 channel (TRPC7$^{DN}$), (mutated amino acids are in bold)
SEQ ID NO: 12 shows the complete nucleotide sequence of TRPC7$^{DN}$; (mutated nucleotides are in bold)

EXAMPLES

1. Construction and Functional Properties of TRPC3$^{DN}$

To study TRPC channel function in vitro and in vivo we used a dominant-negative channel mutant to modulate native TRPC channel activity. The applicability of this approach for TRPC channels had been previously demonstrated (Hofmann et al. (2002) Proc. Natl. Acad. Sci. U.S.A., 99, 7461-7466). We generated a dominant-negative TRPC3 channel (TRPC3$^{DN}$) by exchanging amino acids 621-623 of wild type human TRPC3 (NP_003296) for alanines by site directed mutagenesis. The insert was cloned into a modified pcDNA3 vector backbone using gateway technology (Invitrogen, Karlsruhe, Germany).

A HEK 293 line stably expressing the muscarinic $M_1$-receptor (HM1 cells) was used in this study (Peralta et al. (1988) Nature, 334, 434-437). Cells were grown at 37° C. in DMEM/F12 (1:1) medium supplemented with 10% fetal calf serum, 2 mM glutamine, 100 U/ml penicillin, 100 µg/ml streptomycin (Invitrogen, Karlsruhe, Germany) in 5.5% $CO_2$. G418 (0.5 mg/ml) was added to the growth medium. The cDNAs for hTRPC3 (U47050), hTRPC6 (AF080394), TRPC3$^{DN}$, and eGFP (pEGFP-N1, BD Biosciences, Palo Alto, Calif.) or YFP-tagged versions of the channel proteins were transfected using LipofectAMINE 2000 (Invitrogen, Karlsruhe, Germany) according to the manufacturers' instructions For electrophysiological experiments cells were transfected with the indicated amounts of cDNA in 35 mm dishes and plated onto coverslips 12-24 hrs after transfection. Cells were used 24-48 hrs after plating. If not indicated otherwise 0.4 µg eGFP was co-transfected as expression marker for patch-clamp experiments.

Whole-cell currents were recorded from fluorescent cells at room temperature with a HEKA EPC 10 patch clamp amplifier and PULSE software (HEKA, Lambrecht, Germany). Patch pipettes with resistances of 2-5 MΩ in standard extracellular buffer were pulled from borosilicate glass. The holding potential was set to −70 mV and currents during 160 ms voltage ramps from −100 to +60 mV were sampled with 6.6 kHz. All recordings were filtered at 2 kHz.

Standard external buffer contained (in mM): NaCl 140, KCl 5.4, $CaCl_2$ 2, $MgCl_2$ 1, glucose 10, HEPES 10, and pH was adjusted to 7.4 with NaOH. The standard pipette buffer contained (in mM): CsOH 120, gluconic acid 120, $MgCl_2$ 2, $CaCl_2$ 3, $Cs_4$-BAPTA 5, HEPES 10; pH was adjusted to 7.3 with gluconic acid. Free $[Ca^{2+}]$ was calculated to be ~200 nM using the CaBuf program (G. Droogmans, K U Leuven).

Receptor-activated currents were elicited in HM1 cells by application of 10 μM carbachol.

All statistical data is expressed as means±SEM. Statistical analysis was performed using SigmaStat (SPSS, Chicago, Ill.). Results were pooled and analyzed using the Mann-Whitney rank sum test. The significance level was set to p<0.05.

1.1 TRPC3$^{DN}$ Does Not Carry Functional Ion Currents

To establish that TRPC3$^{DN}$ acts as a negative TRPC channel modulator the functional properties of the channel mutant were investigated by whole cell patch clamp.

Figure 1B:
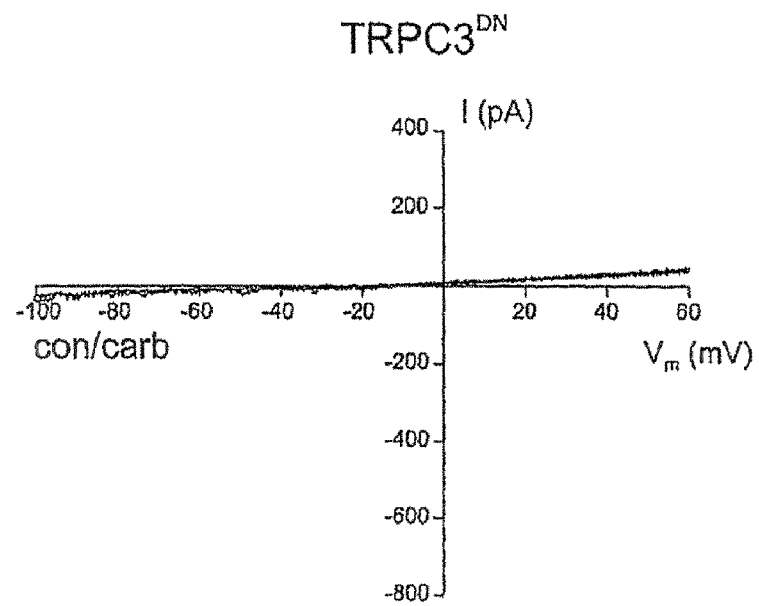

Representative current recordings from HM1 cells transfected with 3 μg TRPC3 or TRPC3$^{DN}$ are shown in FIGS. 1A and 1B. TRPC currents were elicited by the acetylcholine receptor agonist carbachol (10 μM). Currents were recorded before (con) and in the presence of carbachol (carb).

On average the current density of TRPC3$^{DN}$ expressing cells (1,3 pA/pF, n=11) was not different from cells transfected with LacZ as a negative control (1,2 pA/pF, n=10).

In accordance with the recordings shown in FIGS. 1A and 1B cells transfected with TRPC3 as a positive control displayed significantly greater current densities (11,2 pA/pF, n=11; p<0,001). Thus, TRPC3$^{DN}$ did not carry notable ion currents.

Previous studies suggest that TRPC3 directly interacts with itself as well as TRPC6 and TRPC7 (Hofmann et al. (2002) Proc. Natl. Acad. Sci. U.S.A., 99, 7461-7466). Therefore, the modulatory effects of TRPC3$^{DN}$ were tested by co-expression with wild type TRPC3 and TRPC6 channels.

1.2 Dominant-Negative Effect of TRPC3$^{DN}$ on TRPC3 and TRPC6

Figure 2A:
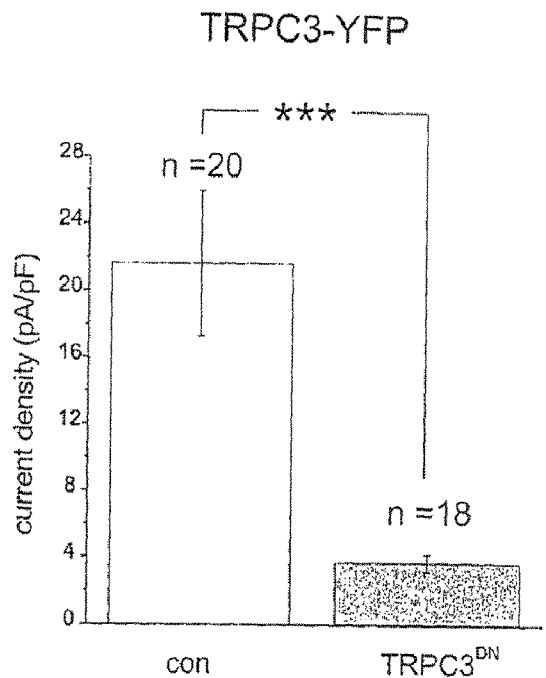
FIGS. 2A and B show the dominant-negative effect of TRPC3$^{DN}$ on TRPC3 and TRPC6

According to FIG. 2A HM1 cells were co-transfected with 7 μg TRPC3-YFP and 7 μg LacZ as control (open bars) or 7 μg TRPC3$^{DN}$ (gray bars). According to FIG. 2B HM1 cells were co-transfected with 7 μg TRPC6-YFP and LacZ or TRPC3$^{DN}$ as in FIG. 2A.

Carbachol-induced currents were measured at −70 mV and normalized to the cell capacitance. TRPC3$^{DN}$ significantly (***p<0.001) suppressed currents through both TRPC3 and TRPC6.

2. Anti-Atherosclerotic Effects of TRPC3$^{DN}$ In Vivo

Figure 2B:
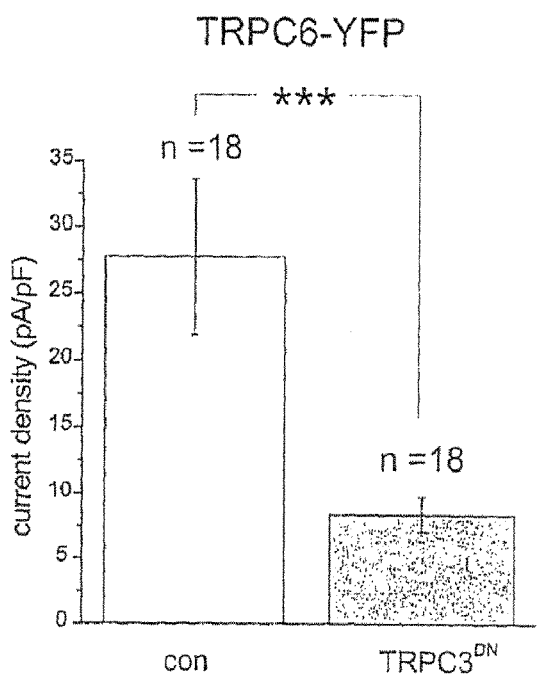

As shown in FIGS. 2A and 2B TRPC3$^{DN}$ conferred a dominant-negative effect on TRPC3 and TRPC6 channels. Based on sequence homology and previous reports (Hofmann et al. (2002), supra) it can be assumed that also the homologous TRPC7 channel is suppressed by TRPC3$^{DN}$. To investigate the effects of TRPC3$^{DN}$ expression and, thus, inhibition of TRPC3, TRPC6, and TRPC7 on atherosclerosis viral gene transfer of TRPC3$^{DN}$ to vessels of atherosclerotic rabbits were used.

Carotid arteries were infected with viruses harbouring TRPC3$^{DN}$ or eGFP as a control. 8 weeks after gene transfer the disease state was evaluated by functional and histological parameters.

2.1 Virus Generation and Animal Studies

Adenoviruses encoding the dominant negative mutant of TPRC3 were generated, amplified and purified at large scale. Subsequently, the correctness of the sequence was checked by DNA sequencing (Medigenomix, Martinsried, Germany) and specific expression of the proteins was confirmed by Western Blotting.

White New Zealand rabbits, 20 weeks of age, were fed on a diet with 1% cholesterol+5% corn oil. After 1 week of feeding, transgene expression was induced by catheter-based viral gene transfer (see below). Cholesterol feeding was continued for the whole course of the experiment. At least 8 animals were independently investigated in each group.

Serum cholesterol levels were assessed before the initiation of feeding, directly before gene transfer, and 2, 4 and 8 weeks after gene transfer. The measurements were carried out in a validated laboratory specialized on veterinarian serum determinations (Synlab, Augsburg, Germany). Also the LDL and HDL subfractions were determined with standard techniques. No significant differences were observed for serum cholesterol, LDL- or HDL cholesterol in control versus TRPC3$^{DN}$ receiving animals (p>0.05) for all time points measured (n=8 each group).

2.2 Endothelial Gene Transfer to the Carotid Artery

For gene transfer to the carotid artery a cervical midline incision was made and the left common artery was exposed. A segment of 4 cm was isolated with two small atraumatic clips (BIEMER vessel clips, FD 561 R). Approximately 0.2 ml TRPC3$^{DN}$ or eGFP virus solution (titer 10$^{10}$ pfu) was injected by a small needle (0.4×20) into the isolated segment. The incubation time was 20 min. Then, the clips were removed and the blood circulation was restored. The cervical wound was sutured and the animal was allowed to recover. The rabbits obtained analgesia (Temgesic®, Buprenorphin 0.01 mg/kg sc. every 12 h) for 72 hours post operation.

2.3 Measurement of Endothelial Vasoreactivity

At the end of the experiment, eight weeks after gene transfer, basal vessel diameter and acetylcholine-induced vasoreactivity were determined by high definition ultrasound of the carotid artery.

Figure 3:
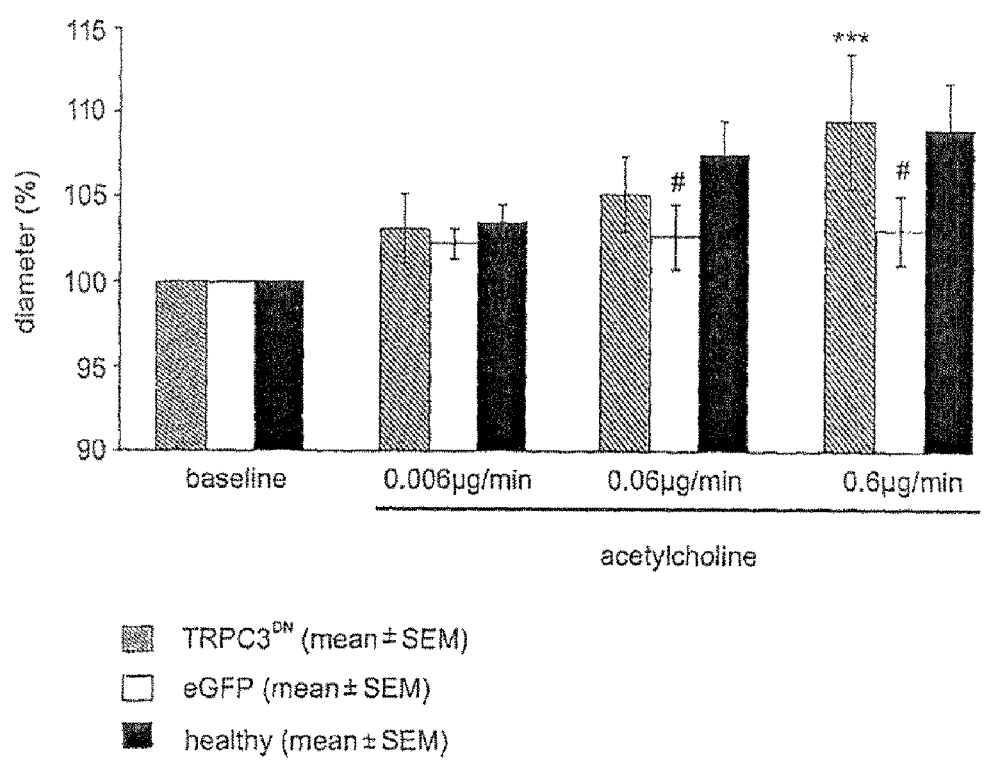
FIG. 3 shows the effect of TRPC3$^{DN}$ on acetylcholine-induced vasoreactivity in carotid arteries of atherosclerotic rabbits

In vivo measurements of luminal vessel diameter was performed on carotid artery segments of atherosclerotic rabbits (FIG. 3) transduced with TRPC3$^{DN}$ (hatched bars) or eGFP (open bars) and in healthy (non-atherosclerotic) rabbits (filled bars). Acetylcholine-induced vasoreactivity was measured 4 times every minute after the injection of the given doses of acetylcholine. TRPC3$^{DN}$ expression significantly improved acetylcholine-induced vasoreactivity compared to eGFP expressing segments (*** p<0.001). A decrease of vasoreactivity was observed in eGFP expressing segments vs. healthy controls (# p<0.01).

Figure 4:
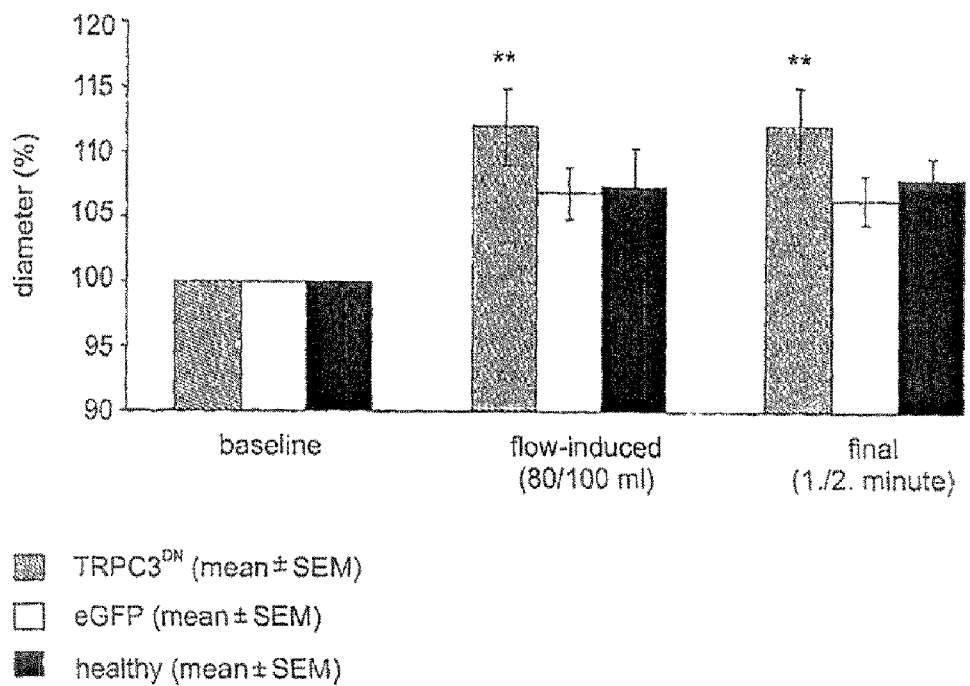
FIG. 4 shows a sonographic assessment of flow-induced vasoreactivity in TRPC3$^{DN}$ expressing carotid artery segments

In a second set of experiments, flow-induced vasoreactivity in response to administration of sodium chloride solution was tested (FIG. 4).

Luminal vessel diameter of carotid artery segments was measured in atherosclerotic rabbits transduced with TRPC3$^{DN}$ (hatched bars) or eGFP (open bars) and in healthy (non-atherosclerotic) rabbits (filled bars). Flow-induced vasoreactivity was tested during administration of 100 ml sodium chloride solution (applied over 5 min). Measurements taken after 80 ml of infusion and 1-2 min after application of the total volume are shown. TRPC3$^{DN}$ expression significantly improved flow-induced vasoreactivity compared to eGFP expressing segments (** p<0.01).

2.4 Determination of Histological Markers of Atherosclerosis

In order to assess disease progression histologically animals were injected with heparin and sacrificed. Carotid arteries were dissected proximally 1 cm from the sternum, distally at the epiglottis. The vessels were flushed with saline, dried carefully and shock frozen. A piece of artery from the central area was excised for investigation of GFP expression, HE and van Gieson staining and immunohistochemistry.

The rest of the artery was used for Sudan macrostaining to detect lipid plaques. For this purpose, sudan red staining was directly induced after perfusing the vessels with saline for 2 minutes and cutting longitudinally in the middle. Thereafter, the vessels were transferred to Sudan stain solution (Sudan III dissolved in alcohol and acetone).

Figure 5:
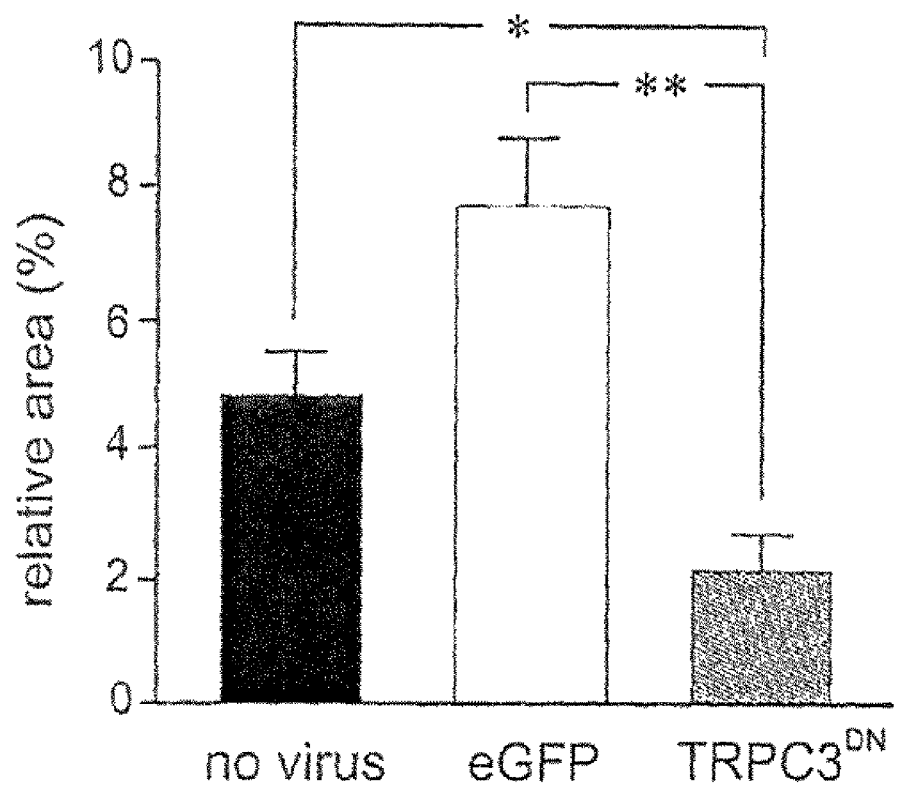
FIG. 5 shows the size of atherosclerotic plaques in TRPC3$^{DN}$ expressing carotid artery segments

Relative plaque size was determined by Sudan red staining followed by histological image analysis of carotid artery segments tranceduced with TRPC3$^{DN}$ or eGFP (FIG. 5). The right carotid arteries from rabbits that received TRPC3$^{DN}$ (to the left arteries) were evaluated as untreated controls. TRPC3$^{DN}$ decreased plaque size vs. both eGFP (**p<0.01) and untreated (*p<0.05) controls.

Figure 6:
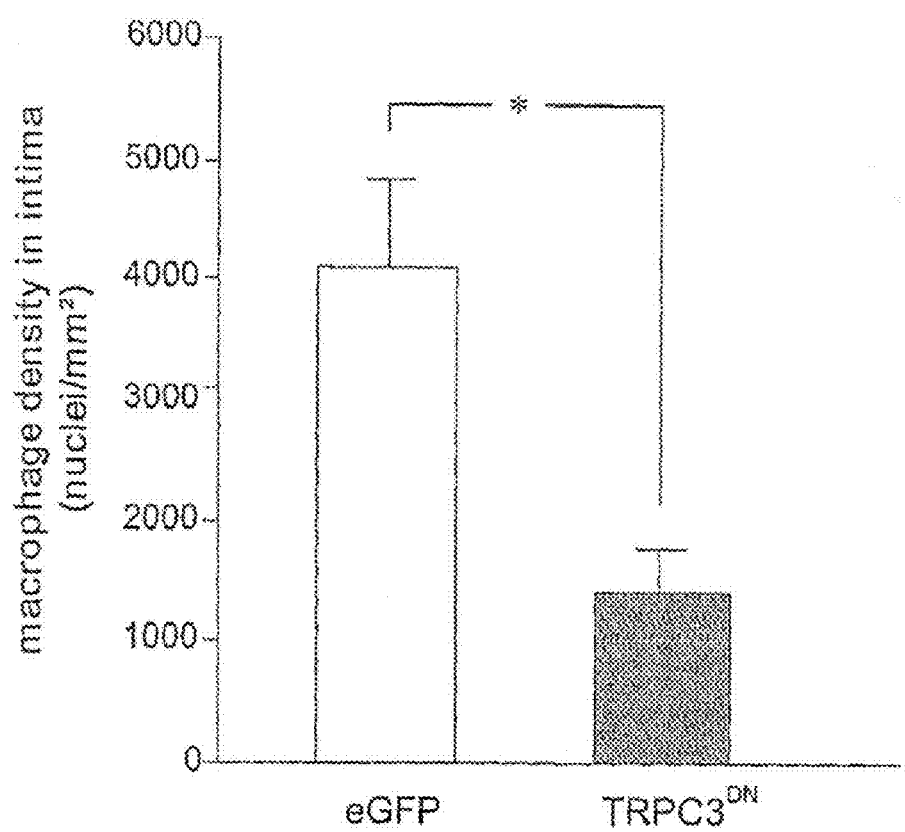
FIG. 6 shows the effect of TRPC3$^{DN}$ expression on mean macrophage density in atherosclerotic carotid arteries

As another marker of atherosclerosis progression macrophage infiltration of the vessel intima was studied by immunocytochemisty. For histological staining, 6 μm slices were cut from the middle of all vessels which had been prepared by removing fat. The slices were fixed with acetone for 10 minutes at room temperature and air dried. They were then permeabilized with 0.6% $H_2O_2$ in 100% methanol for 5 minutes, washed with PBS three times and incubated with 20% rabbit serum. Next the slices were incubated with an anti-macrophage monoclonal antibody (1:100, clone RAM-11, DAKO, Hamburg, Germany) at 20° C. for 20-30 minutes and washed three times with PBS. They were then incubated with the appropriate biotin-labelled secondary antibodies for 30 minutes at 20° C., and again washed three times with PBS. Subsequently slices were incubated with ABC reagent for 30 minutes, washed with PBS, and stained with diaminobenzidine and $H_2O_2$ for 10 minutes. Counterstaining with Harris/hematoxylin/eosin was carried out thereafter. Analysis was performed by directly counting single positive cells in the vessel intima in each slide at high magnification (typically 600-fold) by a standardized counting procedure (FIG. 6).

Macrophages were identified by immunocytochemistry in the intimal layer of carotid arteries expressing TRPC3$^{DN}$ or eGFP. TRPC3$^{DN}$ caused a significant reduction of macrophage infiltration compared to eGFP expressing vessels (*p<0.05).

3. Assay for High Throughput Identification of TRPC3, TRPC6 and TRPC7 Modulators To develop an assay for the identification of TRPC channel modulators, recombinant HEK 293 cell lines were produced using the Flp-In T-REx system (Invitrogen, Karsruhe, Germany) that express TRPC3 (accession # U47050) or TRPC6 (accession # AF080394) cDNAs under the control of an inducible promoter. Channel cDNAs were amplified by standard techniques and cloned into pcDNA5/FRT/TO (Invitrogen, Karlsruhe, Germany). After transfection of Flp-In T-Rex 293 cells with the channel constructs stable cell lines were selected with hygromycin. Cells were maintained according to the manufactures instructions and channel expression of was induced by addition of 1 μg/ml doxycycline for 20-30 h. Cells were plated into 96 well poly-d-lysine coated black walled clear bottom microtiter plates (BD Biosciences, Bedford, Mass.) at a density of 40000-50000 cells/well 20-30 h before experiments. Cell were then washed and loaded with 2 μM fluo4am (Molecular Probes, Eugene, Oreg.) for 30-45 min at room temperature in a buffer containing 1×HBSS (#14065-049, Invitrogen), 1 mM $CaCl_2$, 20 mM HEPES, 0.02% Pluronic F-127 (Molecular Probes), and 0.05% bovine serum albumin (pH=7.4). Loading buffer was removed and cells incubated with test compounds for 10 min at room temperature. $Ca^{2+}$ measurements were performed using a 96 well Fluorescence Imaging Plate Reader (FLIPR), (Molecular Devices Corporation, Sunnyvale, Calif.). To stimulate $Ca^{2+}$ influx through TRPC3 or TRPC6 we applied the channel activator 1-oleyl-2-acetyl-sn-glycerol (OAG) (Hofmann et al., 1999), at a final concentration of 30-50 μM. OAG was dissolved in a buffer containing 1×HBSS (#14065-049, Invitrogen), 1 mM $CaCl_2$, 20 mM HEPES, 0.02% Pluronic F-127 (Molecular Probes) (pH=7.4) and added to the cells. Alternatively, OAG could be dissolved in a buffer containing 1×HBSS (#14065-049, Invitrogen), 1 mM $CaCl_2$, 20 mM HEPES, and 0.1% bovine serum albumin (pH=7.4).

Figure 7A:
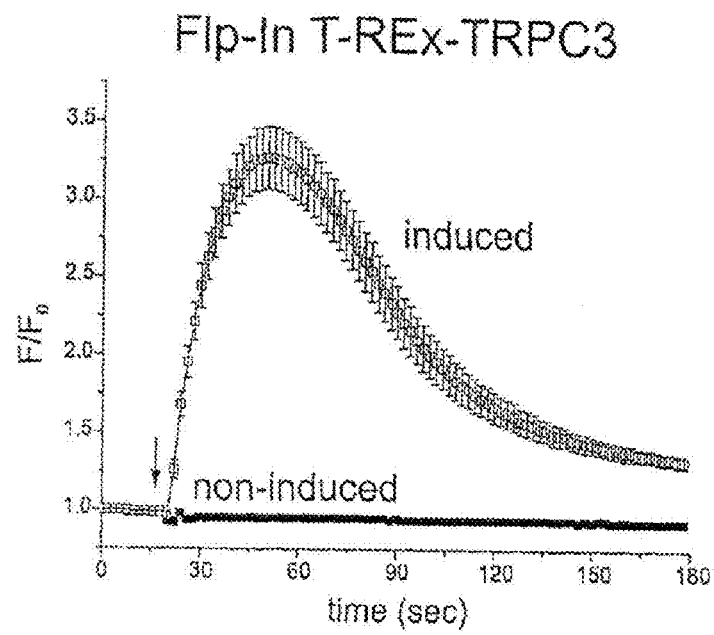
FIGS. 7A and 7B show the detection of OAG-activated $Ca^{2+}$ signals in inducible TRPC3 and TRPC6 cell lines using FLIPR technology
Figure 7B:
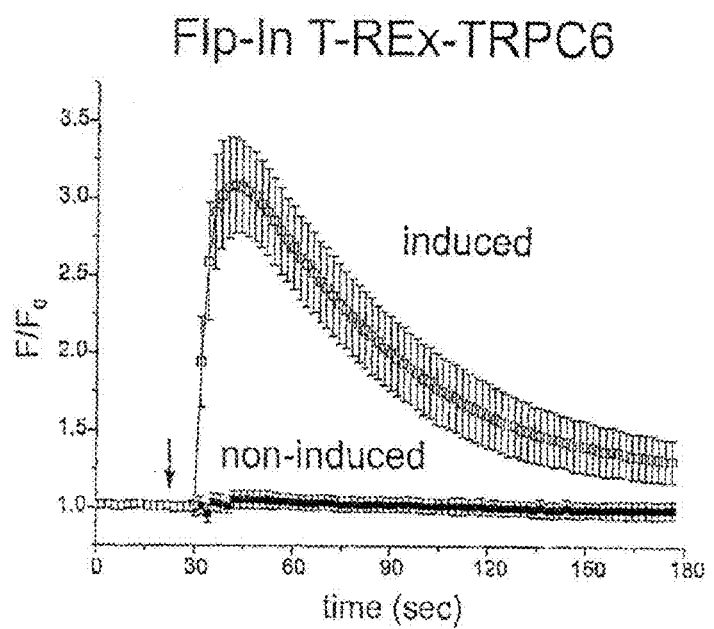

FIGS. 7A and 7B show that responses to OAG were observed only in doxyciclin-treated but not in non-induced cells. Thus, this result demonstrates that the OAG-activated $Ca^{2+}$ signal is specifically mediated by TRPC3 or TRPC6 respectively.

Fluorescence changes in fluo-4 loaded cells were measured using FLIPR II. The bar indicates application of 50 μM OAG. Shown are mean fluorescence values±SEM from 9 wells each. Fluorescence values were normalized to the mean baseline fluorescence ($F_0$).

To identify modulators of TRPC3 or TRPC6 with the assays described above induced cells were used and test compounds are added to the wells before or after application of OAG. The expected effect of inhibitors would be a reduction of the fluorescence increase. Channel activators would lead to a further increase of the OAG-evoked signal or induce an OAG-independent fluorescence increase. SKF 96365 (1-(β-[3-(4 -methoxyphenyl)propoxy]-4-methoxyphenethyl)-1H-imidazole-HCl) has been described as an inhibitor of nonselective cation channels including TRPC3 and TRPC6 (Boulay et al. (1997), J. Biol. Chem., 272, 29672-29680; Zhu et al. (1998), J. Biol. Chem., 273, 133-142).

Figure 8A:
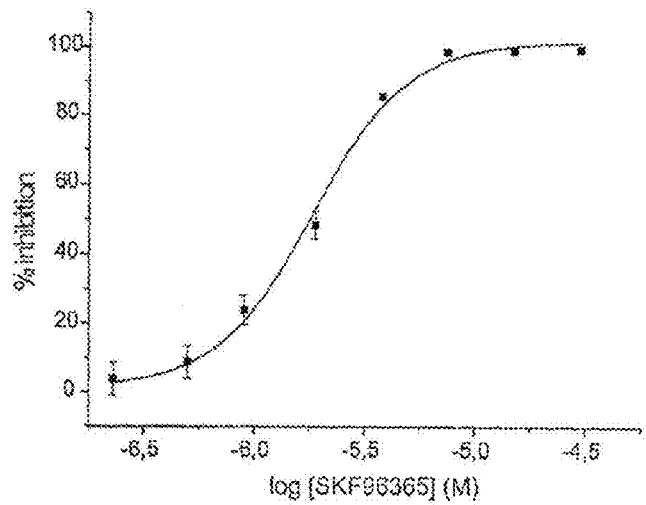
FIGS. 8A and 8B illustrate the $IC_{50}$ for TRPC3 and TRPC6 inhibition by SKF 96365 in doxycycline-induced cell lines by a FLIPR assay
Figure 8B:
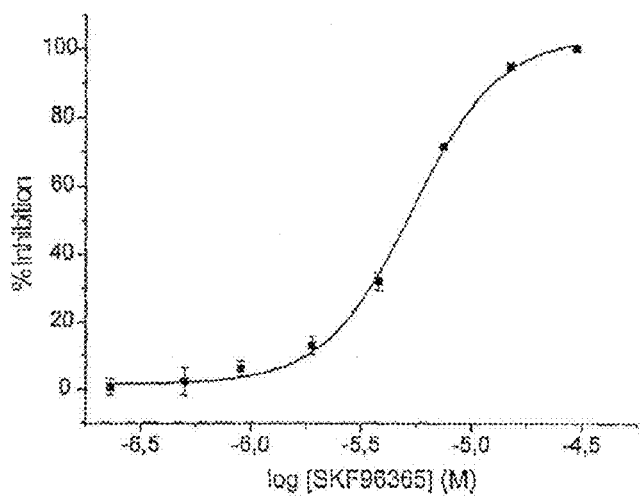

As shown in FIGS. 8A and 8B SKF 96365 inhibited OAG-activated fluorescence responses in TRPC3 expressing cells with an $IC_{50}$ of 1,8±0,12 μM (n=8) and in TRPC6 expressing cells with an $IC_{50}$ of 5.04±0.17 μM (n=8). Thus, the given examples demonstrate the ability of the assays to identify TRPC3 and TRPC6 modulators.

Fluorescence changes induced by 30 μM OAG in TRPC3- and TRPC6 expressing cells were measured in the presence of the given concentrations of SKF 96365. Mean inhibition values±SEM are shown. Inhibition is expressed as % of control fluorescence in the absence of SKF 96365. Dose-response curves were fitted to the general dose-response equation. The spline curves represent the best fits to the composite data.

As an alternative mode of TRPC3 and TRPC6 channel activation the protease-activated receptor agonist trypsin (200 nM) was applied to induced Flp-In T-REx-TRPC3 and Flp-In T-REx-TRPC6 cells. This treatment exemplifies the use of $G_q$-coupled receptor agonists for stimulation of TRPC3 or TRPC6. At t=60 sec after application trypsin induced significantly greater increases in fluorescence in induced Flp-In T-REx-TRPC3 and Flp-In T-REx-TRPC6 cells compared to non-induced controls (Table 1). Hence, $G_q$-coupled receptor agonists, e.g. trypsin, may also be used in the assay to stimulate TRPC3 and TRPC6 responses.

TABLE 1

Fluorescence changes ($F/F_0$) in induced and non-induced Flp-In T-REx-TRPC3 and Flp-In T-REx-TRPC6 cells in response to 200 nM trypsin

|  | Flp-In T-REx-TRPC3 | Flp-In T-REx-TRPC6 |
| --- | --- | --- |
| induced | 2.71 ± 0.022 (n = 9) | 2.26 ± 0.05 (n = 12) |
| non-induced | 1.65 ± 0.034 (n = 9) | 0.88 ± 0.009 (n = 12) |

Values are given as means±SEM. Induced and non-induced groups were significantly different (p<0.001, t-test).

SEQ ID NO: 1
MEGSPSLRRMTVMREKGRRQAVRGPAFMFNDRGTSLTAEEERFLDAAEYGNIPVVRKMLEESKT
LNVNCVDYMGQNALQLAVGNEHLEVTELLLKKENLARIGDALLLAISKGYVRIVEAILNHPGFA
ASKRLTLSPCEQELQDDDFYAYDEDGTRFSPDITPIILAAHCQKYEVVHMLLMKGARIERPHDY
FCKCGDCMEKQRHDSFSHSRSRINAYKGLASPAYLSLSSEDPVLTALELSNELAKLANIEKEFK
NDYRKLSMQCKDFVVGVLDLCRDSEEVEAILNGDLESAEPLEVHRHKASLSRVKLAIKYEVKKF
VAHPNCQQQLLTIWYENLSGLREQTIAIKCLVVLVVALGLPFLAIGYWIAPCSRLGKILRSPFM
KFVAHAASFIIFLGLLVFNASDRFEGITTLPNITVTDYPKQIFRVKTTQFTWTEMLIMVWVLGM
MWSECKELWLEGPREYILQLWNVLDFGMLSIFIAAFTARFLAFLQATKAQQYVDSYVQESDLSE
VTLPPEIQYFTYARDKWLPSDPQIISEGLYAIAVVLSFSRIAYILPANESFGPLQISLGRTVKD
IFKFMVLFIMVFFAFMIGMFILYSYYLGAKVNAAFTTVEESFKTLFWSIFGLSEVTSVVLKYDH
KFIENIGYVLYGIYNVTMVVVLLNMLIAMINSSYQEIEDDSDVEWKFARSKLWLSYFDDGKTLP
PPFSLVPSPKSFVYFIMRIVNFPKCRRRRLQKDIEMGMGNSKSRLNLFTQSNSRVFESHSFNSI
LNQPTRYQQIMKRLIKRYVLKAQVDKENDEVNEGELKEIKQDISSLRYELLEDKSQATEELAIL
IHKLSEKLNPSMLRCE

SEQ ID NO: 2
ATGGAGGGAAGCCCATCCCTGAGACGCATGACAGTGATGCGGGAGAAGGGCCGGCGCCAGGCTG
TCAGGGGCCCGGCCTTCATGTTCAATGACCGCGGCACCAGCCTCACCGCCGAGGAGGAGCGCTT
CCTCGACGCCGCCGAGTACGGCAACATCCCAGTGGTGCGCAAGATGCTGGAGGAGTCCAAGACG
CTGAACGTCAACTGCGTGGACTACATGGGCCAGAACGCGCTGCAGCTGGCTGTGGGCAACGAGC
ACCTGGAGGTGACCGAGCTGCTGCTCAAGAAGGAGAACCTGGCGCGCATTGGCGACGCCCTGCT
GCTCGCCATCAGCAAGGGCTACGTGCGCATTGTAGAGGCCATCCTCAACCACCCTGGCTTCGCG
GCCAGCAAGCGTCTCACTCTGAGCCCCTGTGAGCAGGAGCTGCAGGACGACGACTTCTACGCTT
ACGATGAGGACGGCACGCGCTTCTCGCCGGACATCACCCCCATCATCCTGGCGGCGCACTGCCA
GAAATACGAAGTGGTGCACATGCTGCTGATGAAGGGTGCCAGGATCGAGCGGCCGCACGACTAT
TTCTGCAAGTGCGGGGACTGCATGGAGAAGCAGAGGCACGACTCCTTCAGCCACTCACGCTCGA
GGATCAATGCCTACAAGGGGCTGGCCAGCCCGGCTTACCTCTCATTGTCCAGCGAGGACCCGGT
GCTTACGGCCCTAGAGCTCAGCAACGAGCTGGCCAAGCTGGCCAACATAGAGAAGGAGTTCAAG
AATGACTATCGGAAGCTCTCCATGCAATGCAAAGACTTTGTAGTGGGTGTGCTGGATCTCTGCC
GAGACTCAGAAGAGGTAGAAGCCATTCTGAATGGAGATCTGGAATCAGCAGAGCCTCTGGAGGT
ACACAGGCACAAAGCTTCATTAAGTCGTGTCAAACTTGCCATTAAGTATGAAGTCAAAAAGTTT
GTGGCTCATCCCAACTGCCAGCAGCAGCTCTTGACGATCTGGTATGAGAACCTCTCAGGCCTAA
GGGAGCAGACCATAGCTATCAAGTGTCTCGTTGTGCTGGTCGTGGCCCTGGGCCTTCCATTCCT
GGCCATTGGCTACTGGATCGCACCTTGCAGCAGGCTGGGGAAAATTCTGCGAAGCCCTTTTATG
AAGTTTGTAGCACATGCAGCTTCTTTCATCATCTTCCTGGGTCTGCTTGTGTTCAATGCCTCAG
ACAGGTTCGAAGGCATCACCACGCTGCCCAATATCACAGTTACTGACTATCCCAAACAGATCTT
CAGGGTGAAAACCACCCAGTTTACATGGACTGAAATGCTAATTATGGTCTGGGTTCTTGGAATG
ATGTGGTCTGAATGTAAAGAGCTCTGGCTGGAAGGACCTAGGGAATACATTTTGCAGTTGTGGA
ATGTGCTTGACTTTGGGATGCTGTCCATCTTCATTGCTGCTTTCACAGCCAGATTCCTAGCTTT
CCTTCAGGCAACGAAGGCACAACAGTATGTGGACAGTTACGTCCAAGAGAGTGACCTCAGTGAA
GTGACACTCCCACCAGAGATACAGTATTTCACTTATGCTAGAGATAAATGGCTCCCTTCTGACC
CTCAGATTATATCTGAAGGCCTTTATGCCATAGCTGTTGTGCTCAGCTTCTCTCGGATTGCGTA

-continued

CATCCTCCCTGCAAATGAGAGCTTTGGCCCCCTGCAGATCTCTCTTGGAAGGACTGTAAAGGAC

ATATTCAAGTTCATGGTCCTCTTTATTATGGTGTTTTTTGCCTTTATGATTGGCATGTTCATAC

TTTATTCTTACTACCTTGGGGCTAAAGTTAATGCTGCTTTTACCACTGTAGAAGAAAGTTTCAA

GACTTTATTTTGGTCAATATTTGGGTTGTCTGAAGTGACTTCCGTTGTGCTCAAATATGATCAC

AAATTCATAGAAAATATTGGATACGTTCTTTATGGAATATACAATGTAACTATGGTGGTCGTTT

TACTCAACATGCTAATTGCTATGATTAATAGCTCATATCAAGAAATTGAGGATGACAGTGATGT

AGAATGGAAGTTTGCTCGTTCAAAACTTTGGTTATCCTATTTTGATGATGGAAAAACATTACCT

CCACCTTTCAGTCTAGTTCCTAGTCCAAAATCATTTGTTTATTTCATCATGCGAATTGTTAACT

TTCCCAAATGCAGAAGGAGAAGACTTCAGAAGGATATAGAAATGGGAATGGGTAACTCAAAGTC

CAGGTTAAACCTCTTCACTCAGTCTAACTCAAGAGTTTTTGAATCACACAGTTTTAACAGCATT

CTCAATCAGCCAACACGTTATCAGCAGATAATGAAAAGACTTATAAAGCGGTATGTTTTGAAAG

CACAAGTAGACAAAGAAATGATGAAGTTAATGAAGGTGAATTAAAAGAAATCAAGCAAGATAT

CTCCAGCCTTCGTTATGAACTTTTGGAAGACAAGAGCCAAGCAACTGAGGAATTAGCCATTCTA

ATTCATAAACTTAGTGAGAAACTGAATCCCAGCATGCTGAGATGTGAATGA

SEQ ID NO: 3

MEGSPSLRRMTVMREKGRRQAVRGPAFMFNDRGTSLTAEEERFLDAAEYGNIPVVRKMLEESKT

LNVNCVDYMGQNALQLAVGNEHLEVTELLLKKENLARIGDALLLAISKGYVRIVEAILNHPGFA

ASKRLTLSPCEQELQDDDFYAYDEDGTRFSPDITPIILAAHCQKYEVVHMLLMKGARIERPHDY

FCKCGDCMEKQRHDSFSHSRSRINAYKGLASPAYLSLSSEDPVLTALELSNELAKLANIEKEFK

NDYRKLSMQCKDFVVGVLDLCRDSEEVEAILNGDLESAEPLEVHRHKASLSRVKLAIKYEVKKF

VAHPNCQQQLLTIWYENLSGLREQTIAIKCLVVLVVALGLPFLAIGYWIAPCSRLGKILRSPFM

KFVAHAASFIIFLGLLVFNASDRFEGITTLPNITVTDYPKQIFRVKTTQFTWTEMLIMVWVLGM

MWSECKELWLEGPREYILQLWNVLDFGMLSIFIAAFTARFLAFLQATKAQQYVDSYVQESDLSE

VTLPPEIQYFTYARDKWLPSDPQIISEGLYAIAVVLSFSRIAYILPANESFGPLQISLGRTVKD

IFKFMVLFIMVFFAFMIGMFILYSYYLGAKVNAAFTTVEESFKTAAASIFGLSEVTSVVLKYDH

KFIENIGYVLYGIYNVTMVVVLLNMLIAMINSSYQEIEDDSDVEWKFARSKLWLSYFDDGKTLP

PPFSLVPSPKSFVYFIMRIVNFPKCRRRRLQKDIEMGMGNSKSRLNLFTQSNSRVFESHSFNSI

LNQPTRYQQIMKRLIKRYVLKAQVDKENDEVNEGELKEIKQDISSLRYELLEDKSQATEELAIL

IHKLSEKLNPSMLRCE

SEQ ID NO: 4

ATGGAGGGAAGCCCATCCCTGAGACGCATGACAGTGATGCGGGAGAAGGGCCGGCGCCAGGCTG

TCAGGGGCCCGGCCTTCATGTTCAATGACCGCGGCACCAGCCTCACCGCCGAGGAGGAGCGCTT

CCTCGACGCCGCCGAGTACGGCAACATCCCAGTGGTGCGCAAGATGCTGGAGGAGTCCAAGACG

CTGAACGTCAACTGCGTGGACTACATGGGCCAGAACGCGCTGCAGCTGGCTGTGGGCAACGAGC

ACCTGGAGGTGACCGAGCTGCTGCTCAAGAAGGAGAACCTGGCGCGCATTGGCGACGCCCTGCT

GCTCGCCATCAGCAAGGGCTACGTGCGCATTGTAGAGGCCATCCTCAACCACCCTGGCTTCGCG

GCCAGCAAGCGTCTCACTCTGAGCCCCTGTGAGCAGGAGCTGCAGGACGACGACTTCTACGCTT

ACGATGAGGACGGCACGCGCTTCTCGCCGGACATCACCCCCATCATCCTGGCGGCGCACTGCCA

GAAATACGAAGTGGTGCACATGCTGCTGATGAAGGGTGCCAGGATCGAGCGGCCGCACGACTAT

TTCTGCAAGTGCGGGACTGCATGGAGAAGCAGAGGCACGACTCCTTCAGCCACTCACGCTCGA

GGATCAATGCCTACAAGGGGCTGGCCAGCCCGGCTTACCTCTCATTGTCCAGCGAGGACCCGGT

-continued

```
GCTTACGGCCCTAGAGCTCAGCAACGAGCTGGCCAAGCTGGCCAACATAGAGAAGGAGTTCAAG
AATGACTATCGGAAGCTCTCCATGCAATGCAAAGACTTTGTAGTGGGTGTGCTGGATCTCTGCC
GAGACTCAGAAGAGGTAGAAGCCATTCTGAATGGAGATCTGGAATCAGCAGAGCCTCTGGAGGT
ACACAGGCACAAAGCTTCATTAAGTCGTGTCAAACTTGCCATTAAGTATGAAGTCAAAAAGTTT
GTGGCTCATCCCAACTGCCAGCAGCAGCTCTTGACGATCTGGTATGAGAACCTCTCAGGCCTAA
GGGAGCAGACCATAGCTATCAAGTGTCTCGTTGTGCTGGTCGTGGCCCTGGGCCTTCCATTCCT
GGCCATTGGCTACTGGATCGCACCTTGCAGCAGGCTGGGGAAAATTCTGCGAAGCCCTTTTATG
AAGTTTGTAGCACATGCAGCTTCTTTCATCATCTTCCTGGGTCTGCTTGTGTTCAATGCCTCAG
ACAGGTTCGAAGGCATCACCACGCTGCCCAATATCACAGTTACTGACTATCCCAAACAGATCTT
CAGGGTGAAAACCACCCAGTTTACATGGACTGAAATGCTAATTATGGTCTGGGTTCTTGGAATG
ATGTGGTCTGAATGTAAAGAGCTCTGGCTGGAAGGACCTAGGGAATACATTTTGCAGTTGTGGA
ATGTGCTTGACTTTGGGATGCTGTCCATCTTCATTGCTGCTTTCACAGCCAGATTCCTAGCTTT
CCTTCAGGCAACGAAGGCACAACAGTATGTGGACAGTTACGTCCAAGAGAGTGACCTCAGTGAA
GTGACACTCCCACCAGAGATACAGTATTTCACTTATGCTAGAGATAAATGGCTCCCTTCTGACC
CTCAGATTATATCTGAAGGCCTTTATGCCATAGCTGTTGTGCTCAGCTTCTCTCGGATTGCGTA
CATCCTCCCTGCAAATGAGAGCTTTGGCCCCCTGCAGATCTCTCTTGGAAGGACTGTAAAGGAC
ATATTCAAGTTCATGGTCCTCTTTATTATGGTGTTTTTTGCCTTTATGATTGGCATGTTCATAC
TTTATTCTTACTACCTTGGGGCTAAAGTTAATGCTGCTTTTACCACTGTAGAAGAAAGTTTCAA
GACTGCAGCTGCGTCAATATTTGGGTTGTCTGAAGTGACTTCCGTTGTGCTCAAATATGATCAC
AAATTCATAGAAAATATTGGATACGTTCTTTATGGAATATACAATGTAACTATGGTGGTCGTTT
TACTCAACATGCTAATTGCTATGATTAATAGCTCATATCAAGAAATTGAGGATGACAGTGATGT
AGAATGGAAGTTTGCTCGTTCAAAACTTTGGTTATCCTATTTTGATGATGGAAAAACATTACCT
CCACCTTTCAGTCTAGTTCCTAGTCCAAAATCATTTGTTTATTTCATCATGCGAATTGTTAACT
TTCCCAAATGCAGAAGGAGAAGACTTCAGAAGGATATAGAAATGGGAATGGGTAACTCAAAGTC
CAGGTTAAACCTCTTCACTCAGTCTAACTCAAGAGTTTTTGAATCACACAGTTTTAACAGCATT
CTCAATCAGCCAACACGTTATCAGCAGATAATGAAAAGACTTATAAAGCGGTATGTTTTGAAAG
CACAAGTAGACAAAGAAAATGATGAAGTTAATGAAGGTGAATTAAAAGAAATCAAGCAAGATAT
CTCCAGCCTTCGTTATGAACTTTTGGAAGACAAGAGCCAAGCAACTGAGGAATTAGCCATTCTA
ATTCATAAACTTAGTGAGAAACTGAATCCCAGCATGCTGAGATGTGAATGA
```

SEQ ID NO: 5

```
MSQSPAFGPRRGSSPRGAAGAAARRNESQDYLLMDSELGEDGCPQAPLPCYGYYPCFRGSDNRL
AHRRQTVLREKGRRLANRGPAYMFSDRSTSLSIEEERFLDAAEYGNIPVVRKMLEECHSLNVNC
VDYMGQNALQLAVANEHLEITELLLKKENLSRVGDALLLAISKGYVRIVEAILSHPAFAEGKRL
ATSPSQSELQQDDFYAYDEDGTRFSHDVTPIILAAHCQEYEIVHTLLRKGARIERPHDYFCKCN
DCNQKQKHDSFSHSRSRINAYKGLASPAYLSLSSEDPVMTALELSNELAVLANIEKEFKNDYKK
LSMQCKDFVVGLLDLCRNTEEVEAILNGDVETLQSGDHGRPNLSRLKLAIKYEVKKFVAHPNCQ
QQLLSIWYENLSGLRQQTMAVKFLVVLAVAIGLPFLALIYWFAPCSKMGKIMRGPFMKFVAHAA
SFTIFLGLLVMNAADRFEGTKLLPNETSTDNAKQLFRMKTSCFSWMEMLIISWVIGMIWAECKE
IWTQGPKEYLFELWNMLDFGMLAIFAASFIARFMAFWHASKAQSIIDANDTLKDLTKVTLGDNV
KYYNLARIKWDPSDPQIISEGLYAIAVVLSFSRIAYILPANESFGPLQISLGRTVKDIFKFMVI
FIMVFVAFMIGMFNLYSYYIGAKQNEAFTTVEESFKTLFWAIFGLSEVKSVVINYNHKFIENIG
```

-continued

YVLYGVYNVTMVIVLLNMLIAMINSSFQEIEDDADVEWKFARAKLWFSYFEEGRTLPVPFNLVP

SPKSLFYLLLKLKKWISELFQGHKKGFQEDAEMNKINEEKKLGILGSHEDLSKLSLDKKQVGHN

KQPSIRSSEDFHLNSFNNPPRQYQKIMKRLIKRYVLQAQIDKESDEVNEGELKEIKQDISSLRY

ELLEEKSQNTEDLAELIRELGEKLSMEPNQEETNR

SEQ ID NO: 6

ATGAGCCAGAGCCCGGCGTTCGGGCCCCGGAGGGGCAGTTCTCCCCGGGGCGCTGCCGGAGCCG

CTGCGCGGCGCAACGAGAGCCAGGACTATCTGCTCATGGACTCGGAGCTGGGAGAAGACGGCTG

CCCGCAAGCCCCGCTGCCTTGCTACGGCTACTACCCCTGCTTCCGGGGATCTGACAACAGACTG

GCTCACCGGCGGCAGACAGTTCTCCGTGAGAAGGGGAGAAGGTTAGCTAATCGAGGACCAGCAT

ACATGTTTAGTGATCGCTCCACAAGCCTATCTATAGAGGAGGAACGCTTTTTGGATGCAGCTGA

ATATGGTAACATCCCAGTGGTGCGGAAGATGTTAGAAGAATGCCACTCACTCAACGTTAACTGT

GTGGATTACATGGGCCAGAATGCCCTACAGTTGGCAGTGGCCAATGAGCATCTGGAAATTACAG

AACTTCTTCTCAAGAAAGAAAACCTCTCTCGAGTTGGGGATGCTTTGCTTCTAGCTATTAGTAA

AGGTTATGTTCGGATTGTGGAAGCAATTCTCAGTCATCCGGCTTTTGCTGAAGGCAAGAGGTTA

GCAACCAGCCCTAGCCAGTCTGAACTCCAGCAAGATGATTTTTATGCCTATGATGAAGATGGGA

CACGGTTCTCCCATGATGTGACTCCAATCATTCTGGCTGCCCACTGCCAGGAATATGAAATTGT

GCATACCCTCCTGCGGAAGGGTGCTAGGATTGAACGGCCTCATGATTATTTCTGCAAGTGCAAT

GACTGCAACCAGAAACAGAAGCATGACTCGTTTAGCCACTCCAGATCTAGGATTAATGCCTATA

AAGGCCTGGCAAGTCCGGCTTACCTGTCATTGTCTAGTGAAGATCCAGTCATGACGGCTTTAGA

ACTTAGCAATGAACTGGCAGTTCTGGCCAATATTGAGAAAGAGTTCAAGAATGACTACAAAAAA

CTGTCAATGCAGTGCAAAGACTTTGTTGTTGGACTCCTTGATCTGTGCAGAAACACTGAAGAAG

TCGAGGCCATTCTGAATGGGGATGTTGAAACGCTCCAGAGTGGTGATCACGGTCGCCCAAATCT

CAGCCGTTTAAAACTTGCCATTAAATATGAAGTAAAAAAATTTGTAGCTCATCCAAACTGCCAA

CAGCAACTTCTCTCCATTTGGTATGAGAATCTTTCTGGTTTACGACAGCAGACAATGGCGGTCA

AGTTCCTTGTGGTCCTTGCTGTTGCCATTGGACTGCCCTTCCTGGCTCTCATTTACTGGTTTGC

TCCATGCAGCAAGATGGGGAAGATAATGCGTGGACCATTCATGAAGTTTGTAGCACACGCAGCC

TCCTTCACCATTTTTCTGGGACTGCTAGTCATGAATGCAGCTGACAGATTTGAAGGCACAAAAC

TCCTTCCTAATGAAACCAGCACAGATAATGCAAAACAGCTGTTCAGGATGAAAACATCCTGCTT

CTCATGGATGGAGATGCTCATTATATCCTGGGTAATAGGCATGATATGGGCTGAATGTAAAGAA

ATCTGGACTCAGGGCCCCAAGGAATATTTGTTTGAGTTGTGGAACATGCTTGATTTTGGTATGT

TAGCAATTTTCGCAGCATCATTCATTGCGAGATTCATGGCATTTTGGCATGCTTCCAAAGCCCA

GAGCATCATTGACGCAAACGATACTTTGAAGGACTTGACGAAAGTAACATTGGGAGACAATGTG

AAATACTACAATTTGGCCAGGATAAAGTGGGACCCCTCTGATCCTCAAATAATATCTGAAGGTC

TTTATGCAATTGCTGTAGTTTTAAGTTTCTCTAGGATAGCTTATATTTTACCAGCAAATGAAAG

CTTTGGACCTCTGCAGATATCACTTGGAAGAACAGTCAAAGACATCTTCAAGTTCATGGTCATA

TTCATTATGGTGTTTGTGGCCTTTATGATTGGAATGTTCAATCTCTACTCCTACTACATTGGTG

CAAAACAAAATGAAGCCTTCACAACAGTTGAAGAGAGTTTTAAGACACTGTTCTGGGCTATATT

TGGACTTTCTGAAGTGAAATCAGTGGTCATCAACTATAACCACAAATTCATTGAAAACATTGGT

TACGTTCTTTATGGAGTCTATAATGTTACGATGGTCATTGTTTTGCTAAATATGTTAATTGCCA

TGATCAACAGTTCATTCCAGGAAATTGAGGATGACGCTGATGTGGAGTGGAAATTTGCAAGGGC

CAAACTCTGGTTTTCCTACTTTGAGGAGGGCAGAACACTTCCTGTACCCTTCAATCTGGTGCCG

-continued

```
AGTCCAAAGTCCCTGTTTTATCTCTTACTGAAGCTTAAAAAATGGATTTCTGAGCTGTTCCAGG

GCCATAAAAAAGGTTTCCAGGAAGATGCAGAGATGAACAAGATAAATGAAGAAAAGAAACTTGG

AATTTTAGGAAGTCATGAAGACCTTTCAAAATTATCACTTGACAAAAA

ACAGGTTGGGCACAATAAACAACCAAGTATAAGGAGCTCAGAAGATTTCCATCTAAATAGTTTC

AATAATCCTCCAAGACAATATCAGAAAATAATGAAAAGGCTCATTAAAAGATATGTACTGCAGG

CCCAGATAGATAAGGAGAGTGATGAAGTGAACGAAGGGGAACTGAAGGAAATTAAGCAGGACAT

CTCAAGTCTCCGCTATGAACTCCTTGAAGAAAAATCTCAGAATACAGAAGACCTAGCAGAACTT

ATTAGAGAACTTGGAGAGAAATTATCCATGGAACCAAATCAAGAGGAAACCAATAGATAA
```

SEQ ID NO: 7
```
MSQSPAFGPRRGSSPRGAAGAAARRNESQDYLLMDSELGEDGCPQAPLPCYGYYPCFRGSDNRL

AHRRQTVLREKGRRLANRGPAYMFSDRSTSLSIEEERFLDAAEYGNIPVVRKMLEECHSLNVNC

VDYMGQNALQLAVANEHLEITELLLKKENLSRVGDALLLAISKGYVRIVEAILSHPAFAEGKRL

ATSPSQSELQQDDFYAYDEDGTRFSHDVTPIILAAHCQEYEIVHTLLRKGARIERPHDYFCKCN

DCNQKQKHDSFSHSRSRINAYKGLASPAYLSLSSEDPVMTALELSNELAVLANIEKEFKNDYKK

LSMQCKDFVVGLLDLCRNTEEVEAILNGDVETLQSGDHGRPNLSRLKLAIKYEVKKFVAHPNCQ

QQLLSIWYENLSGLRQQTMAVKFLVVLAVAIGLPFLALIYWFAPCSKMGKIMRGPFMKFVAHAA

SFTIFLGLLVMNAADRFEGTKLLPNETSTDNAKQLFRMKTSCFSWMEMLIISWVIGMIWAECKE

IWTQGPKEYLFELWNMLDFGMLAIFAASFIARFMAFWHASKAQSIIDANDTLKDLTKVTLGDNV

KYYNLARIKWDPSDPQIISEGLYAIAVVLSFSRIAYILPANESFGPLQISLGRTVKDIFKFMVI

FIMVFVAFMIGMFNLYSYYIGAKQNEAFTTVEESFKTAAAAIFGLSEVKSVVINYNHKFIENIG

YVLYGVYNVTMVIVLLNMLIAMINSSFQEIEDDADVEWKFARAKLWFSYFEEGRTLPVPFNLVP

SPKSLFYLLLKLKKWISELFQGHKKGFQEDAEMNKINEEKKLGILGSHEDLSKLSLDKKQVGHN

KQPSIRSSEDFHLNSFNNPPRQYQKIMKRLIKRYVLQAQIDKESDEVNEGELKEIKQDISSLRY

ELLEEKSQNTEDLAELIRELGEKLSMEPNQEETNR
```

SEQ ID NO: 8
```
ATGAGCCAGAGCCCGGCGTTCGGGCCCCGGAGGGGCAGTTCTCCCCGGGGCGCTGCCGGAGCCG

CTGCGCGGCGCAACGAGAGCCAGGACTATCTGCTCATGGACTCGGAGCTGGGAGAAGACGGCTG

CCCGCAAGCCCCGCTGCCTTGCTACGGCTACTACCCCTGCTTCCGGGGATCTGACAACAGACTG

GCTCACCGGCGGCAGACAGTTCTCCGTGAGAAGGGGAGAAGGTTAGCTAATCGAGGACCAGCAT

ACATGTTTAGTGATCGCTCCACAAGCCTATCTATAGAGGAGGAACGCTTTTTGGATGCAGCTGA

ATATGGTAACATCCCAGTGGTGCGGAAGATGTTAGAAGAATGCCACTCACTCAACGTTAACTGT

GTGGATTACATGGGCCAGAATGCCCTACAGTTGGCAGTGGCCAATGAGCATCTGGAAATTACAG

AACTTCTTCTCAAGAAAGAAAACCTCTCTCGAGTTGGGGATGCTTTGCTTCTAGCTATTAGTAA

AGGTTATGTTCGGATTGTGGAAGCAATTCTCAGTCATCCGGCTTTTGCTGAAGGCAAGAGGTTA

GCAACCAGCCCTAGCCAGTCTGAACTCCAGCAAGATGATTTTTATGCCTATGATGAAGATGGGA

CACGGTTCTCCCATGATGTGACTCCAATCATTCTGGCTGCCCACTGCCAGGAATATGAAATTGT

GCATACCCTCCTGCGGAAGGGTGCTAGGATTGAACGGCCTCATGATTATTTCTGCAAGTGCAAT

GACTGCAACCAGAAACAGAAGCATGACTCGTTTAGCCACTCCAGATCTAGGATTAATGCCTATA

AAGGCCTGGCAAGTCCGGCTTACCTGTCATTGTCAGTGAAGATCCAGTCATGACGGCTTTAGA

ACTTAGCAATGAACTGGCAGTTCTGGCCAATATTGAGAAAGAGTTCAAGAATGACTACAAAAAA

CTGTCAATGCAGTGCAAAGACTTTGTTGTTGGACTCCTTGATCTGTGCAGAAACACTGAAGAAG

TCGAGGCCATTCTGAATGGGGATGTTGAAACGCTCCAGAGTGGTGATCACGGTCGCCCAAATCT
```

-continued

```
CAGCCGTTTAAAACTTGCCATTAAATATGAAGTAAAAAAATTTGTAGCTCATCCAAACTGCCAA

CAGCAACTTCTCTCCATTTGGTATGAGAATCTTTCTGGTTTACGACAGCAGACAATGGCGGTCA

AGTTCCTTGTGGTCCTTGCTGTTGCCATTGGACTGCCCTTCCTGGCTCTCATTTACTGGTTTGC

TCCATGCAGCAAGATGGGGAAGATAATGCGTGGACCATTCATGAAGTTTGTAGCACACGCAGCC

TCCTTCACCATTTTTCTGGGACTGCTAGTCATGAATGCAGCTGACAGATTTGAAGGCACAAAAC

TCCTTCCTAATGAAACCAGCACAGATAATGCAAACAGCTGTTCAGGATGAAAACATCCTGCTT

CTCATGGATGGAGATGCTCATTATATCCTGGGTAATAGGCATGATATGGGCTGAATGTAAAGAA

ATCTGGACTCAGGGCCCCAAGGAATATTTGTTTGAGTTGTGGAACATGCTTGATTTTGGTATGT

TAGCAATTTTCGCAGCATCATTCATTGCGAGATTCATGGCATTTTGGCATGCTTCCAAAGCCCA

GAGCATCATTGACGCAAACGATACTTTGAAGGACTTGACGAAAGTAACATTGGGAGACAATGTG

AAATACTACAATTTGGCCAGGATAAAGTGGGACCCCTCTGATCCTCAAATAATATCTGAAGGTC

TTTATGCAATTGCTGTAGTTTTAAGTTTCTCTAGGATAGCTTATATTTTACCAGCAAATGAAAG

CTTTGGACCTCTGCAGATATCACTTGGAAGAACAGTCAAAGACATCTTCAAGTTCATGGTCATA

TTCATTATGGTGTTTGTGGCCTTTATGATTGGAATGTTCAATCTCTACTCCTACTACATTGGTG

CAAAACAAAATGAAGCCTTCACAACAGTTGAAGAGAGTTTTAAGACAGCGGCCGCGGCTATATT

TGGACTTTCTGAAGTGAAATCAGTGGTCATCAACTATAACCACAAATTCATTGAAAACATTGGT

TACGTTCTTTATGGAGTCTATAATGTTACGATGGTCATTGTTTTGCTAAATATGTTAATTGCCA

TGATCAACAGTTCATTCCAGGAAATTGAGGATGACGCTGATGTGGAGTGGAAATTTGCAAGGGC

CAAACTCTGGTTTTCCTACTTTGAGGAGGGCAGAACACTTCCTGTACCCTTCAATCTGGTGCCG

AGTCCAAAGTCCCTGTTTTATCTCTTACTGAAGCTTAAAAAATGGATTTCTGAGCTGTTCCAGG

GCCATAAAAAAGGTTTCCAGGAAGATGCAGAGATGAACAAGATAAATGAAGAAAGAAACTTGG

AATTTTAGGAAGTCATGAAGACCTTTCAAAATTATCACTTGACAAAAA

ACAGGTTGGGCACAATAAACAACCAAGTATAAGGAGCTCAGAAGATTTCCATCTAAATAGTTTC

AATAATCCTCCAAGACAATATCAGAAAATAATGAAAAGGCTCATTAAAAGATATGTACTGCAGG

CCCAGATAGATAAGGAGAGTGATGAAGTGAACGAAGGGGAACTGAAGGAAATTAAGCAGGACAT

CTCAAGTCTCCGCTATGAACTCCTTGAAGAAAATCTCAGAATACAGAAGACCTAGCAGAACTT

ATTAGAGAACTTGGAGAGAAATTATCCATGGAACCAAATCAAGAGGAAACCAATAGATAA
```

SEQ ID NO: 9

MLRNSTFKNMQRRHTTLREKGRRQAIRGPAYMFNEKGTSLTPEEERFLDSAEYGNIPVVRKMLE

ESKTLNFNCVDYMGQNALQLAVGNEHLEVTELLLKKENLARVGDALLLAISKGYVRIVEAILNH

PAFAQGQRLTLSPLEQELRDDDFYAYDEDGTRFSHDITPIILAAHCQEYEIVHILLLKGARIER

PHDYFCKCNECTEKQRKDSFSHSRSRMNAYKGLASAAYLSLSSEDPVLTALELSNELARLANIE

TEFKNDYRKLSMQCKDFVVGVLDLCRDTEEVEAILNGDVNFQVWSDHHRPSLSRIKLAIKYEVK

KFVAHPNCQQQLLTMWYENLSGLRQQSIAVKFLAVFGVSIGLPFLAIAYWIAPCSKLGRTLRSP

FMKFVAHAVSFTIFLGLLVVNASDRFEGVKTLPNETFTDYPKQIFRVKTTQFSWTEMLIMKWVL

GMIWSECKEIWEEGPREYVLHLWNLLDFGMLSIFVASFTARFMAFLKATEAQLYVDQHVQDDTL

HNVSLPPEVAYFTYARDKWWPSDPQIISEGLYAIAVVLSFSRIAYILPANESFGPLQISLGRTV

KDIFKFMVIFIMVFVAFMIGMFNLYSYYRGAKYNPAFTTVEESFKTLFWSIFGLSEVISVVLKY

DHKFIENIGYVLYGVYNVTMVVVLLNMLIAMINNSYQEIEEDADVEWKFARAKLWLSYFDEGRT

-continued

LPAPFNLVPSPKSFYYLIMRIKMCLIKLCKSKAKSCENDLEMGMLNSKFKKTRYQAGMRNSENL

TANNTLSKPTRYQKIMKRLIKRYVLKAQVDRENDEVNEGELKEIKQDISSLRYELLEEKSQATG

ELADLIQQLSEKFGKNLNKDHLRVNKGKDI

SEQ ID NO: 10
ATGTTGAGGAACAGCACCTTCAAAAACATGCAGCGCCGGCACACAACGCTGAGGGAGAAGGGCC

GTCGCCAGGCCATCCGGGGTCCCGCCTACATGTTCAACGAGAAGGGCACCAGTCTGACGCCCGA

GGAGGAGCGCTTCCTGGACTCGGCTGAGTATGGCAACATCCCGGTGGTCCGGAAAATGCTGGAG

GAGTCCAAGACCCTTAACTTCAACTGTGTGGACTACATGGGGCAGAACGCTCTGCAGCTGGCCG

TGGGCAACGAGCACCTAGAGGTCACGGAGCTGCTGCTGAAGAAGGAGAACCTGGCACGGGTGGG

GGACGCGCTGCTGCTGGCCATCAGCAAGGGCTATGTGCGCATCGTGGAGGCCATCCTCAACCAC

CCGGCCTTCGCGCAGGGCCAGCGCCTGACGCTCAGCCCGCTGGAACAGGAGCTGCGCGACGACG

ACTTCTATGCCTACGACGAGGACGGCACGCGCTTCTCCCACGACATCACGCCCATCATCCTGGC

GGCGCACTGCCAGGAGTATGAGATCGTGCACATCCTGCTGCTCAAGGGCGCCCGCATCGAGCGG

CCCCACGACTACTTCTGCAAGTGCAATGAGTGCACCGAGAAACAGCGGAAAGACTCCTTCAGCC

ACTCGCGCTCGCGCATGAACGCCTACAAAGGACTGGCGAGTGCTGCCTACTTGTCCCTGTCCAG

CGAAGACCCTGTCCTCACCGCCCTGGAGCTCAGCAACGAGTTAGCCAGACTAGCCAACATTGAG

ACTGAATTTAAGAACGATTACAGGAAGTTATCTATGCAATGCAAGGATTTTGTAGTGGGCGTGC

TGGACCTGTGCCGAGACACAGAAGAGGTGGAAGCAATTTTAAACGGTGATGTGAACTTCCAAGT

CTGGTCCGACCACCACCGTCCAAGTCTGAGCCGGATCAAACTCGCCATTAAATATGAAGTCAAG

AAGTTCGTTGCTCATCCTAACTGTCAGCAGCAATTGCTTACCATGTGGTATGAAAATCTCTCAG

GCTTACGTCAACAGTCTATCGCTGTGAAATTCCTGGCTGTCTTTGGAGTCTCCATAGGCCTCCC

TTTTCTCGCCATAGCCTATTGGATTGCTCCGTGCAGCAAGCTAGGACGAACCCTGAGGAGCCCT

TTCATGAAGTTTGTAGCTCATGCAGTTTCTTTTACAATCTTCTTGGGATTATTAGTTGTGAATG

CATCTGACCGATTTGAAGGTGTTAAAACCCTGCCAAACGAAACCTTCACAGACTACCCAAAACA

AATCTTCAGAGTGAAAACCACACAGTTCTCCTGGACAGAAATGCTCATTATGAAGTGGGTCTTA

GGAATGATTTGGTCCGAATGCAAGGAAATCTGGGAGGAGGGGCCACGGGAGTACGTGCTGCACT

TGTGGAACCTGCTAGATTTCGGGATGCTGTCCATCTTCGTGGCCTCCTTCACAGCACGCTTCAT

GGCCTTCCTGAAGGCCACGGAGGCACAGCTGTACGTGGACCAGCACGTGCAGGACGACACGCTG

CACAATGTCTCGCTTCCGCCGGAAGTGGCATACTTCACCTACGCCAGGGACAAGTGGTGGCCTT

CAGACCCTCAGATCATATCGGAAGGGCTCTACGCGATAGCCGTCGTGCTGAGCTTCTCTCGCAT

TGCATACATTCTGCCAGCCAACGAGAGTTTTGGGCCCCTGCAGATCTCGCTAGGGAGAACTGTG

AAAGATATCTTCAAGTTCATGGTCATTTTCATCATGGTATTTGTGGCCTTCATGATTGGGATGT

TCAACCTGTACTCTTACTACCGAGGTGCCAAATACAACCCAGCGTTTACAACGGTTGAAGAAAG

TTTTAAAACTTTGTTTTGGTCCATATTCGGCTTATCTGAAGTAATCTCAGTGGTGCTGAAATAC

GACCACAAATTCATCGAGAACATTGGCTACGTTCTCTACGGCGTTTATAACGTCACCATGGTGG

TAGTGTTGCTCAACATGCTAATAGCCATGATAAACAACTCCTATCAGGAAATTGAGGAGGATGC

AGATGTGGAATGGAAGTTCGCCCGAGCAAAACTCTGGCTGTCTTACTTTGATGAAGGAAGAACT

CTACCTGCTCCTTTTAATCTAGTGCCAAGTCCTAAATCATTTTATTATCTCATAATGAGAATCA

AGATGTGCCTCATAAAACTCTGCAAATCTAAGGCCAAAAGCTGTGAAAATGACCTTGAAATGGG

CATGCTGAATTCCAAATTCAAGAAGACTCGCTACCAGGCTGGCATGAGGAATTCTGAAAATCTG

ACAGCAAATAACACTTTGAGCAAGCCCACCAGATACCAGAAAATCATGAAACGGCTCATAAAAA

-continued

GATACGTCCTGAAAGCCCAGGTGGACAGAGAAAATGACGAAGTCAATGAAGGCGAGCTGAAGGA

AATCAAGCAAGATATCTCCAGCCTGCGCTATGAGCTTCTTGAGGAAAA

ATCTCAAGCTACTGGTGAGCTGGCAGACCTGATTCAACAACTCAGCGAGAAGTTTGGAAAGAAC

TTAAACAAAGACCACCTGAGGGTGAACAAGGGCAAAGACATTTAG

SEQ ID NO: 11
MLRNSTFKNMQRRHTTLREKGRRQAIRGPAYMFNEKGTSLTPEEERFLDSAEYGNIPVVRKMLE

ESKTLNFNCVDYMGQNALQLAVGNEHLEVTELLLKKENLARVGDALLLAISKGYVRIVEAILNH

PAFAQGQRLTLSPLEQELRDDDFYAYDEDGTRFSHDITPIILAAHCQEYEIVHILLLKGARIER

PHDYFCKCNECTEKQRKDSFSHSRSRMNAYKGLASAAYLSLSSEDPVLTALELSNELARLANIE

TEFKNDYRKLSMQCKDFVVGVLDLCRDTEEVEAILNGDVNFQVWSDHHRPSLSRIKLAIKYEVK

KFVAHPNCQQQLLTMWYENLSGLRQQSIAVKFLAVFGVSIGLPFLAIAYWIAPCSKLGRTLRSP

FMKFVAHAVSFTIFLGLLVVNASDRFEGVKTLPNETFTDYPKQIFRVKTTQFSWTEMLIMKWVL

GMIWSECKEIWEEGPREYVLHLWNLLDFGMLSIFVASFTARFMAFLKATEAQLYVDQHVQDDTL

HNVSLPPEVAYFTYARDKWWPSDPQIISEGLYAIAVVLSFSRIAYILPANESFGPLQISLGRTV

KDIFKFMVIFIMVFVAFMIGMFNLYSYYRGAKYNPAFTTVEESFKTAAASIFGLSEVISVVLKY

DHKFIENIGYVLYGVYNVTMVVVLLNMLIAMINNSYQEIEEDADVEWKFARAKLWLSYFDEGRT

LPAPFNLVPSPKSFYYLIMRIKMCLIKLCKSKAKSCENDLEMGMLNSKFKKTRYQAGMRNSENL

TANNTLSKPTRYQKIMKRLIKRYVLKAQVDRENDEVNEGELKEIKQDISSLRYELLEEKSQATG

ELADLIQQLSEKFGKNLNKDHLRVNKGKDI

SEQ ID NO: 12
ATGTTGAGGAACAGCACCTTCAAAAACATGCAGCGCCGGCACACAACGCTGAGGGAGAAGGGCC

GTCGCCAGGCCATCCGGGGTCCCGCCTACATGTTCAACGAGAAGGGCACCAGTCTGACGCCCGA

GGAGGAGCGCTTCCTGGACTCGGCTGAGTATGGCAACATCCCGGTGGTCCGGAAAATGCTGGAG

GAGTCCAAGACCCTTAACTTCAACTGTGTGGACTACATGGGGCAGAACGCTCTGCAGCTGGCCG

TGGGCAACGAGCACCTAGAGGTCACGGAGCTGCTGCTGAAGAAGGAGAACCTGGCACGGGTGGG

GGACGCGCTGCTGCTGGCCATCAGCAAGGGCTATGTGCGCATCGTGGAGGCCATCCTCAACCAC

CCGGCCTTCGCGCAGGGCCAGCGCCTGACGCTCAGCCCGCTGGAACAGGAGCTGCGCGACGACG

ACTTCTATGCCTACGACGAGGACGGCACGCGCTTCTCCCACGACATCACGCCCATCATCCTGGC

GGCGCACTGCCAGGAGTATGAGATCGTGCACATCCTGCTGCTCAAGGGCGCCCGCATCGAGCGG

CCCCACGACTACTTCTGCAAGTGCAATGAGTGCACCGAGAAACAGCGGAAAGACTCCTTCAGCC

ACTCGCGCTCGCGCATGAACGCCTACAAAGGACTGGCGAGTGCTGCCTACTTGTCCCTGTCCAG

CGAAGACCCTGTCCTCACCGCCCTGGAGCTCAGCAACGAGTTAGCCAGACTAGCCAACATTGAG

ACTGAATTTAAGAACGATTACAGGAAGTTATCTATGCAATGCAAGGATTTTGTAGTGGGCGTGC

TGGACCTGTGCCGAGACACAGAAGAGGTGGAAGCAATTTTAAACGGTGATGTGAACTTCCAAGT

CTGGTCCGACCACCACCGTCCAAGTCTGAGCCGGATCAAACTCGCCATTAAATATGAAGTCAAG

AAGTTCGTTGCTCATCCTAACTGTCAGCAGCAATTGCTTACCATGTGGTATGAAAATCTCTCAG

GCTTACGTCAACAGTCTATCGCTGTGAAATTCCTGGCTGTCTTTGGAGTCTCCATAGGCCTCCC

TTTTCTCGCCATAGCCTATTGGATTGCTCCGTGCAGCAAGCTAGGACGAACCCTGAGGAGCCCT

TTCATGAAGTTTGTAGCTCATGCAGTTTCTTTTACAATCTTCTTGGGATTATTAGTTGTGAATG

CATCTGACCGATTTGAAGGTGTTAAAACCCTGCCAAACGAAACCTTCACAGACTACCCAAAACA

AATCTTCAGAGTGAAAACCACACAGTTCTCCTGGACAGAAATGCTCATTATGAAGTGGGTCTTA

GGAATGATTTGGTCCGAATGCAAGGAAATCTGGGAGGAGGGGCCACGGGAGTACGTGCTGCACT

```
TGTGGAACCTGCTAGATTTCGGGATGCTGTCCATCTTCGTGGCCTCCTTCACAGCACGCTTCAT

GGCCTTCCTGAAGGCCACGGAGGCACAGCTGTACGTGGACCAGCACGTGCAGGACGACACGCTG

CACAATGTCTCGCTTCCGCCGGAAGTGGCATACTTCACCTACGCCAGGGACAAGTGGTGGCCTT

CAGACCCTCAGATCATATCGGAAGGGCTCTACGCGATAGCCGTCGTGCTGAGCTTCTCTCGCAT

TGCATACATTCTGCCAGCCAACGAGAGTTTTGGGCCCCTGCAGATCTCGCTAGGGAGAACTGTG

AAAGATATCTTCAAGTTCATGGTCATTTTCATCATGGTATTTGTGGCCTTCATGATTGGGATGT

TCAACCTGTACTCTTACTACCGAGGTGCCAAATACAACCCAGCGTTTACAACGGTTGAAGAAAG

TTTTAAAACTGCGGCTGCGTCCATATTCGGCTTATCTGAAGTAATCTCAGTGGTGCTGAAATAC

GACCACAAATTCATCGAGAACATTGGCTACGTTCTCTACGGCGTTTATAACGTCACCATGGTGG

TAGTGTTGCTCAACATGCTAATAGCCATGATAAACAACTCCTATCAGGAAATTGAGGAGGATGC

AGATGTGGAATGGAAGTTCGCCCGAGCAAAACTCTGGCTGTCTTACTTTGATGAAGGAAGAACT

CTACCTGCTCCTTTTAATCTAGTGCCAAGTCCTAAATCATTTTATTATCTCATAATGAGAATCA

AGATGTGCCTCATAAAACTCTGCAAATCTAAGGCCAAAAGCTGTGAAAATGACCTTGAAATGGG

CATGCTGAATTCCAAATTCAAGAAGACTCGCTACCAGGCTGGCATGAGGAATTCTGAAAATCTG

ACAGCAAATAACACTTTGAGCAAGCCCACCAGATACCAGAAAATCATGAAACGGCTCATAAAAA

GATACGTCCTGAAAGCCCAGGTGGACAGAGAAAATGACGAAGTCAATGAAGGCGAGCTGAAGGA

AATCAAGCAAGATATCTCCAGCCTGCGCTATGAGCTTCTTGAGGAAAA

ATCTCAAGCTACTGGTGAGCTGGCAGACCTGATTCAACAACTCAGCGAGAAGTTTGGAAAGAAC

TTAAACAAAGACCACCTGAGGGTGAACAAGGGCAAAGACATTTAG
```

The invention claimed is:

1. A method for improving the vascular function of a mammal with atherosclerosis comprising administering to said mammal a pharmaceutically effective amount of an inactivating mutant of a TRPC6 channel protein, said inactivating mutant comprising the amino acid sequence of SEQ ID NO: 7.

* * * * *

SEQUENCE LISTING

<160> NUMBER OF SEQ ID NOS: 12

<210> SEQ ID NO 1
<211> LENGTH: 848
<212> TYPE: PRT
<213> ORGANISM: Homo sapiens

<400> SEQUENCE: 1

Met Glu Gly Ser Pro Ser Leu Arg Arg Met Thr Val Met Arg Glu Lys
1               5                   10                  15

Gly Arg Arg Gln Ala Val Arg Gly Pro Ala Phe Met Phe Asn Asp Arg
            20                  25                  30

Gly Thr Ser Leu Thr Ala Glu Glu Arg Phe Leu Asp Ala Ala Glu
        35                  40                  45

Tyr Gly Asn Ile Pro Val Val Arg Lys Met Leu Glu Glu Ser Lys Thr
    50                  55                  60

Leu Asn Val Asn Cys Val Asp Tyr Met Gly Gln Asn Ala Leu Gln Leu
65                  70                  75                  80

Ala Val Gly Asn Glu His Leu Glu Val Thr Glu Leu Leu Lys Lys
                85                  90                  95

Glu Asn Leu Ala Arg Ile Gly Asp Ala Leu Leu Leu Ala Ile Ser Lys
            100                 105                 110

Gly Tyr Val Arg Ile Val Glu Ala Ile Leu Asn His Pro Gly Phe Ala
        115                 120                 125

Ala Ser Lys Arg Leu Thr Leu Ser Pro Cys Glu Gln Glu Leu Gln Asp
    130                 135                 140

```
Asp Asp Phe Tyr Ala Tyr Asp Glu Asp Gly Thr Arg Phe Ser Pro Asp
145                 150                 155                 160
Ile Thr Pro Ile Ile Leu Ala Ala His Cys Gln Lys Tyr Glu Val Val
            165                 170                 175
His Met Leu Leu Met Lys Gly Ala Arg Ile Glu Arg Pro His Asp Tyr
                180                 185                 190
Phe Cys Lys Cys Gly Asp Cys Met Glu Lys Gln Arg His Asp Ser Phe
            195                 200                 205
Ser His Ser Arg Ser Arg Ile Asn Ala Tyr Lys Gly Leu Ala Ser Pro
        210                 215                 220
Ala Tyr Leu Ser Leu Ser Ser Glu Asp Pro Val Leu Thr Ala Leu Glu
225                 230                 235                 240
Leu Ser Asn Glu Leu Ala Lys Leu Ala Asn Ile Glu Lys Glu Phe Lys
                245                 250                 255
Asn Asp Tyr Arg Lys Leu Ser Met Gln Cys Lys Asp Phe Val Val Gly
            260                 265                 270
Val Leu Asp Leu Cys Arg Asp Ser Glu Glu Val Glu Ala Ile Leu Asn
        275                 280                 285
Gly Asp Leu Glu Ser Ala Glu Pro Leu Glu Val His Arg His Lys Ala
290                 295                 300
Ser Leu Ser Arg Val Lys Leu Ala Ile Lys Tyr Glu Val Lys Lys Phe
305                 310                 315                 320
Val Ala His Pro Asn Cys Gln Gln Leu Leu Thr Ile Trp Tyr Glu
            325                 330                 335
Asn Leu Ser Gly Leu Arg Glu Gln Thr Ile Ala Ile Lys Cys Leu Val
                340                 345                 350
Val Leu Val Val Ala Leu Gly Leu Pro Phe Leu Ala Ile Gly Tyr Trp
            355                 360                 365
Ile Ala Pro Cys Ser Arg Leu Gly Lys Ile Leu Arg Ser Pro Phe Met
        370                 375                 380
Lys Phe Val Ala His Ala Ala Ser Phe Ile Ile Phe Leu Gly Leu Leu
385                 390                 395                 400
Val Phe Asn Ala Ser Asp Arg Phe Glu Gly Ile Thr Thr Leu Pro Asn
                405                 410                 415
Ile Thr Val Thr Asp Tyr Pro Lys Gln Ile Phe Arg Val Lys Thr Thr
            420                 425                 430
Gln Phe Thr Trp Thr Glu Met Leu Ile Met Val Trp Val Leu Gly Met
        435                 440                 445
Met Trp Ser Glu Cys Lys Glu Leu Trp Leu Glu Gly Pro Arg Glu Tyr
450                 455                 460
Ile Leu Gln Leu Trp Asn Val Leu Asp Phe Gly Met Leu Ser Ile Phe
465                 470                 475                 480
Ile Ala Ala Phe Thr Ala Arg Phe Leu Ala Phe Leu Gln Ala Thr Lys
            485                 490                 495
Ala Gln Gln Tyr Val Asp Ser Tyr Val Gln Glu Ser Asp Leu Ser Glu
                500                 505                 510
Val Thr Leu Pro Pro Glu Ile Gln Tyr Phe Thr Tyr Ala Arg Asp Lys
            515                 520                 525
Trp Leu Pro Ser Asp Pro Gln Ile Ile Ser Glu Gly Leu Tyr Ala Ile
        530                 535                 540
Ala Val Val Leu Ser Phe Ser Arg Ile Ala Tyr Ile Leu Pro Ala Asn
545                 550                 555                 560
Glu Ser Phe Gly Pro Leu Gln Ile Ser Leu Gly Arg Thr Val Lys Asp
```

```
                    565                 570                 575
Ile Phe Lys Phe Met Val Leu Phe Ile Met Val Phe Ala Phe Met
                580                 585                 590

Ile Gly Met Phe Ile Leu Tyr Ser Tyr Tyr Leu Gly Ala Lys Val Asn
            595                 600                 605

Ala Ala Phe Thr Thr Val Glu Glu Ser Phe Lys Thr Leu Phe Trp Ser
            610                 615                 620

Ile Phe Gly Leu Ser Glu Val Thr Ser Val Leu Lys Tyr Asp His
625                 630                 635                 640

Lys Phe Ile Glu Asn Ile Gly Tyr Val Leu Tyr Gly Ile Tyr Asn Val
                645                 650                 655

Thr Met Val Val Val Leu Leu Asn Met Leu Ile Ala Met Ile Asn Ser
            660                 665                 670

Ser Tyr Gln Glu Ile Glu Asp Asp Ser Asp Val Glu Trp Lys Phe Ala
            675                 680                 685

Arg Ser Lys Leu Trp Leu Ser Tyr Phe Asp Asp Gly Lys Thr Leu Pro
            690                 695                 700

Pro Pro Phe Ser Leu Val Pro Ser Pro Lys Ser Phe Val Tyr Phe Ile
705                 710                 715                 720

Met Arg Ile Val Asn Phe Pro Lys Cys Arg Arg Arg Leu Gln Lys
                725                 730                 735

Asp Ile Glu Met Gly Met Gly Asn Ser Lys Ser Arg Leu Asn Leu Phe
            740                 745                 750

Thr Gln Ser Asn Ser Arg Val Phe Glu Ser His Ser Phe Asn Ser Ile
            755                 760                 765

Leu Asn Gln Pro Thr Arg Tyr Gln Gln Ile Met Lys Arg Leu Ile Lys
            770                 775                 780

Arg Tyr Val Leu Lys Ala Gln Val Asp Lys Glu Asn Asp Glu Val Asn
785                 790                 795                 800

Glu Gly Glu Leu Lys Glu Ile Lys Gln Asp Ile Ser Ser Leu Arg Tyr
                805                 810                 815

Glu Leu Leu Glu Asp Lys Ser Gln Ala Thr Glu Glu Leu Ala Ile Leu
            820                 825                 830

Ile His Lys Leu Ser Glu Lys Leu Asn Pro Ser Met Leu Arg Cys Glu
            835                 840                 845

<210> SEQ ID NO 2
<211> LENGTH: 2547
<212> TYPE: DNA
<213> ORGANISM: Homo sapiens

<400> SEQUENCE: 2
atggagggaa gcccatccct gagacgcatg acagtgatgc gggagaaggg ccggcgccag      60
gctgtcaggg gcccggcctt catgttcaat gaccgcggca ccagcctcac cgccgaggag     120
gagcgcttcc tcgacgccgc cgagtacggc aacatcccag tggtgcgcaa gatgctggag     180
gagtccaaga cgctgaacgt caactgcgtg gactacatgg ccagaacgc gctgcagctg     240 gctgtgggca cgagcacct ggaggtgacc gagctgctgc tcaagaagga gaacctggcg     300
cgcattggcg acgccctgct gctcgccatc agcaagggct acgtgcgcat tgtagaggcc     360
atcctcaacc accctggctt cgcggccagc aagcgtctca ctctgagccc ctgtgagcag     420
gagctgcagg acgacgactt ctacgcttac gatgaggacg gcacgcgctt ctcgccggac     480 atcacccca tcatcctggc ggcgcactgc cagaaatacg aagtggtgca catgctgctg     540
atgaagggtg ccaggatcga gcggccgcac gactatttct gcaagtgcgg ggactgcatg     600
```

```
gagaagcaga ggcacgactc cttcagccac tcacgctcga ggatcaatgc ctacaagggg      660
ctggccagcc cggcttacct ctcattgtcc agcgaggacc cggtgcttac ggccctagag      720
ctcagcaacg agctggccaa gctggccaac atagagaagg agttcaagaa tgactatcgg      780
aagctctcca tgcaatgcaa agactttgta gtgggtgtgc tggatctctg ccgagactca      840
gaagaggtag aagccattct gaatggagat ctggaatcag cagagcctct ggaggtacac      900
aggcacaaag cttcattaag tcgtgtcaaa cttgccatta gtatgaagt caaaaagttt       960 gtggctcatc ccaactgcca gcagcagctc ttgacgatct ggtatgagaa cctctcaggc     1020
ctaagggagc agaccatagc tatcaagtgt ctcgttgtgc tggtcgtggc cctgggcctt     1080
ccattcctgg ccattggcta ctggatcgca ccttgcagca ggctggggaa aattctgcga     1140 agcccttta tgaagtttgt agcacatgca gcttctttca tcatcttcct gggtctgctt      1200
gtgttcaatg cctcagacag gttcgaaggc atcaccacgc tgcccaatat cacagttact     1260
gactatccca acagatcttc agggtgaaa accacccagt ttacatggac tgaaatgcta      1320
attatggtct gggttcttgg aatgatgtgg tctgaatgta agagctctg gctggaagga      1380 cctagggaat acattttgca gttgtggaat gtgcttgact tgggatgct gtccatcttc       1440 attgctgctt tcacagccag attcctagct ttccttcagg caacgaaggc acaacagtat     1500
gtggacagtt acgtccaaga gagtgacctc agtgaagtga cactcccacc agagatacag     1560
tatttcactt atgctagaga taaatggctc ccttctgacc ctcagattat atctgaaggc     1620
ctttatgcca tagctgttgt gctcagcttc tctcggattg cgtacatcct ccctgcaaat     1680
gagagctttg gcccctgca gatctctctt ggaaggactg taaaggacat attcaagttc      1740
atggtcctct ttattatggt gttttttgcc tttatgattg gcatgttcat actttattct      1800
tactaccttg gggctaaagt taatgctgct tttaccactg tagaagaaag tttcaagact     1860 ttatttggt caatatttgg gttgtctgaa gtgacttccg ttgtgctcaa atatgatcac       1920
aaattcatag aaaatattgg atacgttctt tatggaatat acaatgtaac tatggtggtc     1980
gttttactca acatgctaat tgctatgatt aatagctcat atcaagaaat tgaggatgac     2040
agtgatgtag aatggaagtt tgctcgttca aaactttggt tatcctattt tgatgatgga     2100
aaaacattac ctccacccttt cagtctagtt cctagtccaa atcatttgt ttatttcatc     2160 atgcgaattg ttaactttcc caaatgcaga aggagaagac ttcagaagga tatagaaatg     2220
ggaatgggta actcaaagtc caggttaaac ctcttcactc agtctaactc aagagttttt     2280
gaatcacaca gttttaacag cattctcaat cagccaacac gttatcagca gataatgaaa     2340
agacttataa agcggtatgt tttgaaagca caagtagaca agaaaaatga tgaagttaat     2400
gaaggtgaat taaagaaat caagcaagat atctccagcc ttcgttatga acttttggaa       2460
gacaagagcc aagcaactga ggaattagcc attctaattc ataaacttag tgagaaactg     2520
aatcccagca tgctgagatg tgaatga                                         2547
```

<210> SEQ ID NO 3
<211> LENGTH: 848
<212> TYPE: PRT
<213> ORGANISM: Artificial Sequence
<220> FEATURE:
<223> OTHER INFORMATION: Description of Artificial Sequence: mutant

<400> SEQUENCE: 3

Met Glu Gly Ser Pro Ser Leu Arg Arg Met Thr Val Met Arg Glu Lys
 1               5                  10                  15

-continued

```
Gly Arg Arg Gln Ala Val Arg Gly Pro Ala Phe Met Phe Asn Asp Arg
                 20                  25                  30

Gly Thr Ser Leu Thr Ala Glu Glu Arg Phe Leu Asp Ala Ala Glu
             35                  40                  45

Tyr Gly Asn Ile Pro Val Val Arg Lys Met Leu Glu Glu Ser Lys Thr
         50                  55                  60

Leu Asn Val Asn Cys Val Asp Tyr Met Gly Gln Asn Ala Leu Gln Leu
 65                  70                  75                  80

Ala Val Gly Asn Glu His Leu Glu Val Thr Glu Leu Leu Leu Lys Lys
                 85                  90                  95

Glu Asn Leu Ala Arg Ile Gly Asp Ala Leu Leu Leu Ala Ile Ser Lys
                100                 105                 110

Gly Tyr Val Arg Ile Val Glu Ala Ile Leu Asn His Pro Gly Phe Ala
            115                 120                 125

Ala Ser Lys Arg Leu Thr Leu Ser Pro Cys Glu Gln Glu Leu Gln Asp
130                 135                 140

Asp Asp Phe Tyr Ala Tyr Asp Glu Asp Gly Thr Arg Phe Ser Pro Asp
145                 150                 155                 160

Ile Thr Pro Ile Ile Leu Ala Ala His Cys Gln Lys Tyr Glu Val Val
                165                 170                 175

His Met Leu Leu Met Lys Gly Ala Arg Ile Glu Arg Pro His Asp Tyr
            180                 185                 190

Phe Cys Lys Cys Gly Asp Cys Met Glu Lys Gln Arg His Asp Ser Phe
        195                 200                 205

Ser His Ser Arg Ser Arg Ile Asn Ala Tyr Lys Gly Leu Ala Ser Pro
    210                 215                 220

Ala Tyr Leu Ser Leu Ser Ser Glu Asp Pro Val Leu Thr Ala Leu Glu
225                 230                 235                 240

Leu Ser Asn Glu Leu Ala Lys Leu Ala Asn Ile Glu Lys Glu Phe Lys
                245                 250                 255

Asn Asp Tyr Arg Lys Leu Ser Met Gln Cys Lys Asp Phe Val Val Gly
            260                 265                 270

Val Leu Asp Leu Cys Arg Asp Ser Glu Glu Val Glu Ala Ile Leu Asn
        275                 280                 285

Gly Asp Leu Glu Ser Ala Glu Pro Leu Glu Val His Arg His Lys Ala
    290                 295                 300

Ser Leu Ser Arg Val Lys Leu Ala Ile Lys Tyr Glu Val Lys Lys Phe
305                 310                 315                 320

Val Ala His Pro Asn Cys Gln Gln Leu Leu Thr Ile Trp Tyr Glu
                325                 330                 335

Asn Leu Ser Gly Leu Arg Glu Gln Thr Ile Ala Ile Lys Cys Leu Val
            340                 345                 350

Val Leu Val Val Ala Leu Gly Leu Pro Phe Leu Ala Ile Gly Tyr Trp
        355                 360                 365

Ile Ala Pro Cys Ser Arg Leu Gly Lys Ile Leu Arg Ser Pro Phe Met
    370                 375                 380

Lys Phe Val Ala His Ala Ala Ser Phe Ile Ile Phe Leu Gly Leu Leu
385                 390                 395                 400

Val Phe Asn Ala Ser Asp Arg Phe Glu Gly Ile Thr Thr Leu Pro Asn
                405                 410                 415

Ile Thr Val Thr Asp Tyr Pro Lys Gln Ile Phe Arg Val Lys Thr Thr
            420                 425                 430

Gln Phe Thr Trp Thr Glu Met Leu Ile Met Val Trp Val Leu Gly Met
        435                 440                 445
```

```
Met Trp Ser Glu Cys Lys Glu Leu Trp Leu Glu Gly Pro Arg Glu Tyr
    450                 455                 460

Ile Leu Gln Leu Trp Asn Val Leu Asp Phe Gly Met Leu Ser Ile Phe
465                 470                 475                 480

Ile Ala Ala Phe Thr Ala Arg Phe Leu Ala Phe Leu Gln Ala Thr Lys
                    485                 490                 495

Ala Gln Gln Tyr Val Asp Ser Tyr Val Gln Glu Ser Asp Leu Ser Glu
                500                 505                 510

Val Thr Leu Pro Pro Glu Ile Gln Tyr Phe Thr Tyr Ala Arg Asp Lys
                515                 520                 525

Trp Leu Pro Ser Asp Pro Gln Ile Ile Ser Glu Gly Leu Tyr Ala Ile
                530                 535                 540

Ala Val Val Leu Ser Phe Ser Arg Ile Ala Tyr Ile Leu Pro Ala Asn
545                 550                 555                 560

Glu Ser Phe Gly Pro Leu Gln Ile Ser Leu Gly Arg Thr Val Lys Asp
                565                 570                 575

Ile Phe Lys Phe Met Val Leu Phe Ile Met Val Phe Phe Ala Phe Met
                580                 585                 590

Ile Gly Met Phe Ile Leu Tyr Ser Tyr Tyr Leu Gly Ala Lys Val Asn
                595                 600                 605

Ala Ala Phe Thr Thr Val Glu Glu Ser Phe Lys Thr Ala Ala Ala Ser
610                 615                 620

Ile Phe Gly Leu Ser Glu Val Thr Ser Val Val Leu Lys Tyr Asp His
625                 630                 635                 640

Lys Phe Ile Glu Asn Ile Gly Tyr Val Leu Tyr Gly Ile Tyr Asn Val
                645                 650                 655

Thr Met Val Val Val Leu Leu Asn Met Leu Ile Ala Met Ile Asn Ser
                660                 665                 670

Ser Tyr Gln Glu Ile Glu Asp Asp Ser Asp Val Glu Trp Lys Phe Ala
                675                 680                 685

Arg Ser Lys Leu Trp Leu Ser Tyr Phe Asp Asp Gly Lys Thr Leu Pro
690                 695                 700

Pro Pro Phe Ser Leu Val Pro Ser Pro Lys Ser Phe Val Tyr Phe Ile
705                 710                 715                 720

Met Arg Ile Val Asn Phe Pro Lys Cys Arg Arg Arg Arg Leu Gln Lys
                725                 730                 735

Asp Ile Glu Met Gly Met Gly Asn Ser Lys Ser Arg Leu Asn Leu Phe
                740                 745                 750

Thr Gln Ser Asn Ser Arg Val Phe Glu Ser His Ser Phe Asn Ser Ile
                755                 760                 765

Leu Asn Gln Pro Thr Arg Tyr Gln Gln Ile Met Lys Arg Leu Ile Lys
                770                 775                 780

Arg Tyr Val Leu Lys Ala Gln Val Asp Lys Glu Asn Asp Glu Val Asn
785                 790                 795                 800

Glu Gly Glu Leu Lys Glu Ile Lys Gln Asp Ile Ser Ser Leu Arg Tyr
                805                 810                 815

Glu Leu Leu Glu Asp Lys Ser Gln Ala Thr Glu Glu Leu Ala Ile Leu
                820                 825                 830

Ile His Lys Leu Ser Glu Lys Leu Asn Pro Ser Met Leu Arg Cys Glu
                835                 840                 845

<210> SEQ ID NO 4
<211> LENGTH: 2547
<212> TYPE: DNA
```

<213> ORGANISM: Artificial Sequence
<220> FEATURE:
<223> OTHER INFORMATION: Description of Artificial Sequence: mutant

<400> SEQUENCE: 4

```
atggagggaa gcccatccct gagacgcatg acagtgatgc gggagaaggg ccggcgccag      60
gctgtcaggg gcccggcctt catgttcaat gaccgcggca ccagcctcac cgccgaggag     120
gagcgcttcc tcgacgccgc cgagtacggc aacatcccag tggtgcgcaa gatgctggag     180
gagtccaaga cgctgaacgt caactgcgtg gactacatgg ccagaacgc gctgcagctg      240
gctgtgggca acgagcacct ggaggtgacc gagctgctgc tcaagaagga gaacctggcg     300
cgcattggcg acgccctgct gctcgccatc agcaagggct acgtgcgcat tgtagaggcc     360
atcctcaacc ccctggcttc gcggccagc aagcgtctca ctctgagccc ctgtgagcag      420
gagctgcagg acgacgactt ctacgcttac gatgaggacg gcacgcgctt ctcgccggac     480
atcacccca tcatcctggc ggcgcactgc cagaaatacg aagtggtgca catgctgctg      540
atgaagggtg ccaggatcga gcggccgcac gactatttct gcaagtgcgg ggactgcatg     600
gagaagcaga ggcacgactc cttcagccac tcacgctcga ggatcaatgc ctacaagggg     660
ctggccagcc cggcttacct ctcattgtcc agcgaggacc cggtgcttac ggccctagag     720
ctcagcaacg agctggccaa gctggccaac atagagaagg agttcaagaa tgactatcgg     780
aagctctcca tgcaatgcaa agactttgta gtgggtgtgc tggatctctg ccgagactca     840
gaagaggtag aagccattct gaatggagat ctggaatcag cagagcctct ggaggtacac     900
aggcacaaag cttcattaag tcgtgtcaaa cttgccatta gtatgaagt caaaaagttt      960
gtggctcatc ccaactgcca gcagcagctc ttgacgatct ggtatgagaa cctctcaggc    1020
ctaagggagc agaccatagc tatcaagtgt ctcgttgtgc tggtcgtggc cctgggcctt    1080
ccattcctgg ccattggcta ctggatcgca ccttgcagca ggctggggaa aattctgcga    1140
agccctttta tgaagtttgt agcacatgca gcttctttca tcatcttcct gggtctgctt    1200
gtgttcaatg cctcagacag gttcgaaggc atcaccacgc tgcccaatat cacagttact    1260
gactatccca acagatcttc agggtgaaa accacccagt ttacatggac tgaaatgcta    1320
attatggtct gggttcttgg aatgatgtgg tctgaatgta agagctctg gctggaagga     1380
cctagggaat acatttttgca gttgtggaat gtgcttgact tgggatgct gtccatcttc    1440
attgctgctt tcacagccag attcctagct ttccttcagg caacgaaggc acaacagtat    1500
gtggacagtt acgtccaaga gagtgacctc agtgaagtga cactcccacc agagatacag    1560
tatttcactt atgctagaga taaatggctc ccttctgacc ctcagattat atctgaaggc    1620
ctttatgcca tagctgttgt gctcagcttc tctcggattg cgtacatcct ccctgcaaat    1680
gagagctttg gcccctgca gatctctctt ggaaggactg taaaggacat attcaagttc    1740
atggtcctct ttattatggt gttttttgcc tttatgattg gcatgttcat actttattct    1800
tactaccttg gggctaaagt taatgctgct tttaccactg tagaagaaag tttcaagact    1860
gcagctgcgt caatatttgg gttgtctgaa gtgacttccg ttgtgctcaa atatgatcac    1920
aaattcatag aaaatattgg atacgttctt tatggaatat acaatgtaac tatggtggtc    1980
gttttactca acatgctaat tgctatgatt aatagctcat atcaagaaat tgaggatgac    2040
agtgatgtag aatggaagtt tgctcgttca aaactttggt tatcctattt tgatgatgga    2100
aaaacattac ctcacccttt cagtctagtt cctagtccaa aatcatttgt ttatttcatc    2160
atgcgaattg ttaactttcc caaatgcaga aggagaagac ttcagaagga tatagaaatg    2220
```

```
ggaatgggta actcaaagtc caggttaaac ctcttcactc agtctaactc aagagttttt    2280
gaatcacaca gttttaacag cattctcaat cagccaacac gttatcagca gataatgaaa    2340
agacttataa agcggtatgt tttgaaagca caagtagaca aagaaaatga tgaagttaat    2400
gaaggtgaat taaagaaat caagcaagat atctccagcc ttcgttatga acttttggaa     2460
gacaagagcc aagcaactga ggaattagcc attctaattc ataaacttag tgagaaactg    2520
aatcccagca tgctgagatg tgaatga                                         2547
```

<210> SEQ ID NO 5
<211> LENGTH: 931
<212> TYPE: PRT
<213> ORGANISM: Homo sapiens

<400> SEQUENCE: 5

```
Met Ser Gln Ser Pro Ala Phe Gly Pro Arg Gly Ser Ser Pro Arg
 1               5                  10                  15

Gly Ala Gly Ala Ala Ala Arg Arg Asn Glu Ser Gln Asp Tyr Leu
                20                  25                  30

Leu Met Asp Ser Glu Leu Gly Glu Asp Gly Cys Pro Gln Ala Pro Leu
            35                  40                  45

Pro Cys Tyr Gly Tyr Tyr Pro Cys Phe Arg Gly Ser Asp Asn Arg Leu
        50                  55                  60

Ala His Arg Arg Gln Thr Val Leu Arg Glu Lys Gly Arg Leu Ala
 65                  70                  75                  80

Asn Arg Gly Pro Ala Tyr Met Phe Ser Asp Arg Ser Thr Ser Leu Ser
                85                  90                  95

Ile Glu Glu Glu Arg Phe Leu Asp Ala Ala Glu Tyr Gly Asn Ile Pro
            100                 105                 110

Val Val Arg Lys Met Leu Glu Glu Cys His Ser Leu Asn Val Asn Cys
        115                 120                 125

Val Asp Tyr Met Gly Gln Asn Ala Leu Gln Leu Ala Val Ala Asn Glu
    130                 135                 140

His Leu Glu Ile Thr Glu Leu Leu Leu Lys Lys Glu Asn Leu Ser Arg
145                 150                 155                 160

Val Gly Asp Ala Leu Leu Leu Ala Ile Ser Lys Gly Tyr Val Arg Ile
                165                 170                 175

Val Glu Ala Ile Leu Ser His Pro Ala Phe Ala Glu Gly Lys Arg Leu
            180                 185                 190

Ala Thr Ser Pro Ser Gln Ser Glu Leu Gln Gln Asp Asp Phe Tyr Ala
        195                 200                 205

Tyr Asp Glu Asp Gly Thr Arg Phe Ser His Asp Val Thr Pro Ile Ile
    210                 215                 220

Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
                245                 250                 255

Asp Cys Asn Gln Lys Gln Lys His Asp Ser Phe Ser His Ser Arg Ser
            260                 265                 270

Arg Ile Asn Ala Tyr Lys Gly Leu Ala Ser Pro Ala Tyr Leu Ser Leu
        275                 280                 285

Ser Ser Glu Asp Pro Val Met Thr Ala Leu Glu Leu Ser Asn Glu Leu
    290                 295                 300

Ala Val Leu Ala Asn Ile Glu Lys Glu Phe Lys Asn Asp Tyr Lys Lys
305                 310                 315                 320
```

```
Leu Ser Met Gln Cys Lys Asp Phe Val Gly Leu Leu Asp Leu Cys
            325                 330                 335

Arg Asn Thr Glu Glu Val Glu Ala Ile Leu Asn Gly Asp Val Glu Thr
            340                 345                 350

Leu Gln Ser Gly Asp His Gly Arg Pro Asn Leu Ser Arg Leu Lys Leu
            355                 360                 365

Ala Ile Lys Tyr Glu Val Lys Lys Phe Val Ala His Pro Asn Cys Gln
        370                 375                 380

Gln Gln Leu Leu Ser Ile Trp Tyr Glu Asn Leu Ser Gly Leu Arg Gln
385                 390                 395                 400

Gln Thr Met Ala Val Lys Phe Leu Val Val Leu Ala Val Ala Ile Gly
            405                 410                 415

Leu Pro Phe Leu Ala Leu Ile Tyr Trp Phe Ala Pro Cys Ser Lys Met
            420                 425                 430

Gly Lys Ile Met Arg Gly Pro Phe Met Lys Phe Val Ala His Ala Ala
            435                 440                 445

Ser Phe Thr Ile Phe Leu Gly Leu Leu Val Met Asn Ala Ala Asp Arg
        450                 455                 460

Phe Glu Gly Thr Lys Leu Leu Pro Asn Glu Thr Ser Thr Asp Asn Ala
465                 470                 475                 480

Lys Gln Leu Phe Arg Met Lys Thr Ser Cys Phe Ser Trp Met Glu Met
            485                 490                 495

Leu Ile Ile Ser Trp Val Ile Gly Met Ile Trp Ala Glu Cys Lys Glu
            500                 505                 510

Ile Trp Thr Gln Gly Pro Lys Glu Tyr Leu Phe Glu Leu Trp Asn Met
        515                 520                 525

Leu Asp Phe Gly Met Leu Ala Ile Phe Ala Ala Ser Phe Ile Ala Arg
        530                 535                 540

Phe Met Ala Phe Trp His Ala Ser Lys Ala Gln Ser Ile Ile Asp Ala
545                 550                 555                 560

Asn Asp Thr Leu Lys Asp Leu Thr Lys Val Thr Leu Gly Asp Asn Val
            565                 570                 575

Lys Tyr Tyr Asn Leu Ala Arg Ile Lys Trp Asp Pro Ser Asp Pro Gln
            580                 585                 590

Ile Ile Ser Glu Gly Leu Tyr Ala Ile Ala Val Val Leu Ser Phe Ser
        595                 600                 605

Arg Ile Ala Tyr Ile Leu Pro Ala Asn Glu Ser Phe Gly Pro Leu Gln
            610                 615                 620

Ile Ser Leu Gly Arg Thr Val Lys Asp Ile Phe Lys Phe Met Val Ile
625                 630                 635                 640

Phe Ile Met Val Phe Val Ala Phe Met Ile Gly Met Phe Asn Leu Tyr
            645                 650                 655

Ser Tyr Tyr Ile Gly Ala Lys Gln Asn Glu Ala Phe Thr Thr Val Glu
            660                 665                 670

Glu Ser Phe Lys Thr Leu Phe Trp Ala Ile Phe Gly Leu Ser Glu Val
        675                 680                 685

Lys Ser Val Val Ile Asn Tyr Asn His Lys Phe Ile Glu Asn Ile Gly
        690                 695                 700

Tyr Val Leu Tyr Gly Val Tyr Asn Val Thr Met Val Ile Val Leu Leu
705                 710                 715                 720

Asn Met Leu Ile Ala Met Ile Asn Ser Ser Phe Gln Glu Ile Glu Asp
            725                 730                 735

Asp Ala Asp Val Glu Trp Lys Phe Ala Arg Ala Lys Leu Trp Phe Ser
            740                 745                 750
```

```
Tyr Phe Glu Glu Gly Arg Thr Leu Pro Val Pro Phe Asn Leu Val Pro
        755                 760                 765

Ser Pro Lys Ser Leu Phe Tyr Leu Leu Leu Lys Leu Lys Lys Trp Ile
    770                 775                 780

Ser Glu Leu Phe Gln Gly His Lys Lys Gly Phe Gln Glu Asp Ala Glu
785                 790                 795                 800

Met Asn Lys Ile Asn Glu Glu Lys Lys Leu Gly Ile Leu Gly Ser His
                805                 810                 815

Glu Asp Leu Ser Lys Leu Ser Leu Asp Lys Lys Gln Val Gly His Asn
            820                 825                 830

Lys Gln Pro Ser Ile Arg Ser Glu Asp Phe His Leu Asn Ser Phe
        835                 840                 845

Asn Asn Pro Pro Arg Gln Tyr Gln Lys Ile Met Lys Arg Leu Ile Lys
        850                 855                 860

Arg Tyr Val Leu Gln Ala Gln Ile Asp Lys Glu Ser Asp Val Asn
865                 870                 875                 880

Glu Gly Glu Leu Lys Glu Ile Lys Gln Asp Ile Ser Ser Leu Arg Tyr
                885                 890                 895

Glu Leu Leu Glu Glu Lys Ser Gln Asn Thr Glu Asp Leu Ala Glu Leu
            900                 905                 910

Ile Arg Glu Leu Gly Lys Leu Ser Met Glu Pro Asn Gln Glu Glu
        915                 920                 925

Thr Asn Arg
    930

<210> SEQ ID NO 6
<211> LENGTH: 2796
<212> TYPE: DNA
<213> ORGANISM: Homo sapiens

<400> SEQUENCE: 6
atgagccaga gccggcgtt cgggccccgg aggggcagtt ctccccgggg cgctgccgga      60
gccgctgcgc ggcgcaacga gagccaggac tatctgctca tggactcgga gctgggagaa     120
gacggctgcc gcaagcccc gctgccttgc tacggctact acccctgctt ccggggatct     180
gacaacagag tggctcaccg gcggcagaca gttctccgtg agaaggggag aaggttagct     240
aatcgaggac cagcatacat gtttagtgat cgctccacaa gcctatctat agaggaggaa     300
cgcttttggg atgcagctga atatggtaac atcccagtgg tgcggaagat gttagaagaa     360
tgccactcac tcaacgttaa ctgtgtggat tacatgggcc agaatgccct acagttggca     420
gtggccaatg agcatctgga aattacagaa cttcttctca gaaagaaaaa cctctctcga     480
gttggggatg ctttgcttct agctattagt aaaggttatg ttcggattgt ggaagcaatt     540
ctcagtcatc cggcttttgc tgaaggcaag aggttagcaa ccagccctag ccagtctgaa     600
ctccagcaag atgattttta tgcctatgat gaagatggga cacggttctc ccatgatgtg     660
actccaatca ttctggctgc ccactgccag gaatatgaaa ttgtgcatac cctcctgcgg     720
aagggtgcta ggattgaacg gcctcatgat tatttctgca gtgcaatga ctgcaaccag     780 aaacagaagc atgactcgtt tagccactcc agatctagga ttaatgccta taaggcctg     840 gcaagtccgg cttacctgtc attgtctagt gaagatccag tcatgacggc tttagaactt     900
agcaatgaac tggcagttct ggccaatatt gagaaagagt tcaagaatga ctacaaaaaa    960
ctgtcaatgc agtgcaaaga ctttgttgtt ggactccttg atctgtgcag aaacactgaa   1020
gaagtcgagg ccattctgaa tgggatgtt gaaacgctcc agagtggtga tcacggtcgc   1080
```

```
ccaaatctca gccgtttaaa acttgccatt aaatatgaag taaaaaaatt tgtagctcat   1140
ccaaactgcc aacagcaact tctctccatt tggtatgaga atctttctgg tttacgacag   1200
cagacaatgg cggtcaagtt ccttgtggtc cttgctgttg ccattggact gcccttcctg   1260
gctctcattt actggtttgc tccatgcagc aagatgggga agataatgcg tggaccattc   1320
atgaagtttg tagcacacgc agcctccttc accattttc tgggactgct agtcatgaat   1380
gcagctgaca gatttgaagg cacaaaactc cttcctaatg aaaccagcac agataatgca   1440
aaacagctgt tcaggatgaa acatcctgc ttctcatgga tggagatgct cattatatcc   1500
tgggtaatag gcatgatatg gctgaatgt aaagaaatct ggactcaggg ccccaaggaa   1560
tatttgtttg agttgtggaa catgcttgat tttggtatgt tagcaattt cgcagcatca   1620 ttcattgcga gattcatggc attttggcat gcttccaaag cccagagcat cattgacgca   1680
aacgatactt tgaaggactt gacgaaagta acattgggag acaatgtgaa atactacaat   1740
ttggccagga taaagtggga cccctctgat cctcaaataa tatctgaagg tctttatgca   1800
attgctgtag ttttaagttt ctctaggata gcttatattt taccagcaaa tgaaagcttt   1860
ggacctctgc agatatcact tggaagaaca gtcaaagaca tcttcaagtt catggtcata   1920
ttcattatgg tgtttgtggc ctttatgatt ggaatgttca atctctactc ctactacatt   1980
ggtgcaaaac aaaatgaagc cttcacaaca gttgaagaga gttttaagac actgttctgg   2040
gctatatttg actttctga agtgaaatca gtggtcatca actataacca caaattcatt   2100
gaaaacattg gttacgttct ttatggagtc tataatgtta cgatggtcat tgtttttgcta   2160 aatatgttaa ttgccatgat caacagttca ttccaggaaa ttgaggatga cgctgatgtg   2220
gagtggaaat ttgcaagggc caaactctgg ttttcctact tgaggaggg cagaacactt   2280 cctgtaccct tcaatctggt gccgagtcca aagtccctgt tttatctctt actgaagctt   2340
aaaaaatgga tttctgagct gttccagggc cataaaaaag gttccagga agatgcagag   2400 atgaacaaga taaatgaaga aaagaaactt ggaatttag gaagtcatga agacctttca   2460
aaattatcac ttgacaaaaa acaggttggg cacaataaac aaccaagtat aaggagctca   2520
gaagatttcc atctaaatag tttcaataat cctccaagac aatatcagaa ataatgaaa   2580 aggctcatta aaagatatgt actgcaggcc cagatagata aggagagtga tgaagtgaac   2640 gaagggaac tgaaggaaat taagcaggac atctcaagtc tccgctatga actccttgaa   2700
gaaaaatctc agaatacaga agacctagca gaacttatta gagaacttgg agagaaatta   2760
tccatggaac caaatcaaga ggaaaccaat agataa                             2796

<210> SEQ ID NO 7
<211> LENGTH: 931
<212> TYPE: PRT
<213> ORGANISM: Artificial Sequence
<220> FEATURE:
<223> OTHER INFORMATION: Description of Artificial Sequence: mutant

<400> SEQUENCE: 7

Met Ser Gln Ser Pro Ala Phe Gly Pro Arg Arg Gly Ser Ser Pro Arg
 1               5                  10                  15

Gly Ala Ala Gly Ala Ala Ala Arg Arg Asn Glu Ser Gln Asp Tyr Leu
            20                  25                  30

Leu Met Asp Ser Glu Leu Gly Glu Asp Gly Cys Pro Gln Ala Pro Leu
        35                  40                  45

Pro Cys Tyr Gly Tyr Tyr Pro Cys Phe Arg Gly Ser Asp Asn Arg Leu
    50                  55                  60
```

-continued

```
Ala His Arg Arg Gln Thr Val Leu Arg Glu Lys Gly Arg Arg Leu Ala
 65                  70                  75                  80

Asn Arg Gly Pro Ala Tyr Met Phe Ser Asp Arg Ser Thr Ser Leu Ser
                 85                  90                  95

Ile Glu Glu Glu Arg Phe Leu Asp Ala Ala Tyr Gly Asn Ile Pro
            100                 105                 110

Val Val Arg Lys Met Leu Glu Glu Cys His Ser Leu Asn Val Asn Cys
        115                 120                 125

Val Asp Tyr Met Gly Gln Asn Ala Leu Gln Leu Ala Val Ala Asn Glu
    130                 135                 140

His Leu Glu Ile Thr Glu Leu Leu Leu Lys Lys Glu Asn Leu Ser Arg
145                 150                 155                 160

Val Gly Asp Ala Leu Leu Leu Ala Ile Ser Lys Gly Tyr Val Arg Ile
                165                 170                 175

Val Glu Ala Ile Leu Ser His Pro Ala Phe Ala Glu Gly Lys Arg Leu
            180                 185                 190

Ala Thr Ser Pro Ser Gln Ser Glu Leu Gln Gln Asp Asp Phe Tyr Ala
        195                 200                 205

Tyr Asp Glu Asp Gly Thr Arg Phe Ser His Asp Val Thr Pro Ile Ile
    210                 215                 220

Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
                245                 250                 255

Asp Cys Asn Gln Lys Gln Lys His Asp Ser Phe Ser His Ser Arg Ser
            260                 265                 270

Arg Ile Asn Ala Tyr Lys Gly Leu Ala Ser Pro Ala Tyr Leu Ser Leu
        275                 280                 285

Ser Ser Glu Asp Pro Val Met Thr Ala Leu Glu Leu Ser Asn Glu Leu
    290                 295                 300

Ala Val Leu Ala Asn Ile Glu Lys Glu Phe Lys Asn Asp Tyr Lys Lys
305                 310                 315                 320

Leu Ser Met Gln Cys Lys Asp Phe Val Val Gly Leu Leu Asp Leu Cys
                325                 330                 335

Arg Asn Thr Glu Glu Val Glu Ala Ile Leu Asn Gly Asp Val Glu Thr
            340                 345                 350

Leu Gln Ser Gly Asp His Gly Arg Pro Asn Leu Ser Arg Leu Lys Leu
        355                 360                 365

Ala Ile Lys Tyr Glu Val Lys Lys Phe Val Ala His Pro Asn Cys Gln
    370                 375                 380

Gln Gln Leu Leu Ser Ile Trp Tyr Glu Asn Leu Ser Gly Leu Arg Gln
385                 390                 395                 400

Gln Thr Met Ala Val Lys Phe Leu Val Val Leu Ala Val Ala Ile Gly
                405                 410                 415

Leu Pro Phe Leu Ala Leu Ile Tyr Trp Phe Ala Pro Cys Ser Lys Met
            420                 425                 430

Gly Lys Ile Met Arg Gly Pro Phe Met Lys Phe Val Ala His Ala Ala
        435                 440                 445

Ser Phe Thr Ile Phe Leu Gly Leu Leu Val Met Asn Ala Ala Asp Arg
    450                 455                 460

Phe Glu Gly Thr Lys Leu Leu Pro Asn Glu Thr Ser Thr Asp Asn Ala
465                 470                 475                 480

Lys Gln Leu Phe Arg Met Lys Thr Ser Cys Phe Ser Trp Met Glu Met
```

```
                    485             490             495
Leu Ile Ile Ser Trp Val Ile Gly Met Ile Trp Ala Glu Cys Lys Glu
                500                 505                 510

Ile Trp Thr Gln Gly Pro Lys Glu Tyr Leu Phe Glu Leu Trp Asn Met
        515                 520                 525

Leu Asp Phe Gly Met Leu Ala Ile Phe Ala Ala Ser Phe Ile Ala Arg
530                 535                 540

Phe Met Ala Phe Trp His Ala Ser Lys Ala Gln Ser Ile Ile Asp Ala
545                 550                 555                 560

Asn Asp Thr Leu Lys Asp Leu Thr Lys Val Thr Leu Gly Asp Asn Val
                565                 570                 575

Lys Tyr Tyr Asn Leu Ala Arg Ile Lys Trp Asp Pro Ser Asp Pro Gln
                580                 585                 590

Ile Ile Ser Glu Gly Leu Tyr Ala Ile Ala Val Val Leu Ser Phe Ser
                595                 600                 605

Arg Ile Ala Tyr Ile Leu Pro Ala Asn Glu Ser Phe Gly Pro Leu Gln
            610                 615                 620

Ile Ser Leu Gly Arg Thr Val Lys Asp Ile Phe Lys Phe Met Val Ile
625                 630                 635                 640

Phe Ile Met Val Phe Val Ala Phe Met Ile Gly Met Phe Asn Leu Tyr
                645                 650                 655

Ser Tyr Tyr Ile Gly Ala Lys Gln Asn Glu Ala Phe Thr Thr Val Glu
                660                 665                 670

Glu Ser Phe Lys Thr Ala Ala Ala Ile Phe Gly Leu Ser Glu Val
                675                 680                 685

Lys Ser Val Val Ile Asn Tyr Asn His Lys Phe Ile Glu Asn Ile Gly
            690                 695                 700

Tyr Val Leu Tyr Gly Val Tyr Asn Val Thr Met Val Ile Val Leu Leu
705                 710                 715                 720

Asn Met Leu Ile Ala Met Ile Asn Ser Ser Phe Gln Glu Ile Glu Asp
                725                 730                 735

Asp Ala Asp Val Glu Trp Lys Phe Ala Arg Ala Lys Leu Trp Phe Ser
                740                 745                 750

Tyr Phe Glu Glu Gly Arg Thr Leu Pro Val Pro Phe Asn Leu Val Pro
            755                 760                 765

Ser Pro Lys Ser Leu Phe Tyr Leu Leu Leu Lys Leu Lys Lys Trp Ile
        770                 775                 780

Ser Glu Leu Phe Gln Gly His Lys Lys Gly Phe Gln Glu Asp Ala Glu
785                 790                 795                 800

Met Asn Lys Ile Asn Glu Glu Lys Lys Leu Gly Ile Leu Gly Ser His
                805                 810                 815

Glu Asp Leu Ser Lys Leu Ser Leu Asp Lys Lys Gln Val Gly His Asn
        820                 825                 830

Lys Gln Pro Ser Ile Arg Ser Ser Glu Asp Phe His Leu Asn Ser Phe
        835                 840                 845

Asn Asn Pro Pro Arg Gln Tyr Gln Lys Ile Met Lys Arg Leu Ile Lys
    850                 855                 860

Arg Tyr Val Leu Gln Ala Gln Ile Asp Lys Glu Ser Asp Glu Val Asn
865                 870                 875                 880

Glu Gly Glu Leu Lys Glu Ile Lys Gln Asp Ile Ser Ser Leu Arg Tyr
                885                 890                 895

Glu Leu Leu Glu Glu Lys Ser Gln Asn Thr Glu Asp Leu Ala Glu Leu
                900                 905                 910
```

Ile Arg Glu Leu Gly Glu Lys Leu Ser Met Glu Pro Asn Gln Glu Glu
    915                 920                 925

Thr Asn Arg
    930

<210> SEQ ID NO 8
<211> LENGTH: 2796
<212> TYPE: DNA
<213> ORGANISM: Artificial Sequence
<220> FEATURE:
<223> OTHER INFORMATION: Description of Artificial Sequence: mutant

<400> SEQUENCE: 8

| | | | | | |
|---|---|---|---|---|---|
| atgagccaga | gcccggcgtt | cgggccccgg | aggggcagtt | ctccccgggg | cgctgccgga | 60 |
| gccgctgcgc | ggcgcaacga | gagccaggac | tatctgctca | tggactcgga | gctgggagaa | 120 |
| gacggctgcc | cgcaagcccc | gctgccttgc | tacggctact | accctgctt | ccggggatct | 180 |
| gacaacagag | tggctcaccg | gcggcagaca | gttctccgtg | agaaggggag | aaggttagct | 240 |
| aatcgaggac | cagcatacat | gtttagtgat | cgctccacaa | gcctatctat | agaggaggaa | 300 |
| cgctttttgg | atgcagctga | atatggtaac | atcccagtgg | tgcggaagat | gttagaagaa | 360 |
| tgccactcac | tcaacgttaa | ctgtgtggat | tacatgggcc | agaatgccct | acagttggca | 420 |
| gtggccaatg | agcatctgga | aattacagaa | cttcttctca | agaaagaaaa | cctctctcga | 480 |
| gttggggatg | ctttgcttct | agctattagt | aaaggttatg | ttcggattgt | ggaagcaatt | 540 |
| ctcagtcatc | cggcttttgc | tgaaggcaag | aggttagcaa | ccagccctag | ccagtctgaa | 600 |
| ctccagcaag | atgatttta | tgcctatgat | gaagatggga | cacggttctc | ccatgatgtg | 660 |
| actccaatca | ttctggctgc | ccactgccag | gaatatgaaa | ttgtgcatac | cctcctgcgg | 720 |
| aagggtgcta | ggattgaacg | gcctcatgat | tatttctgca | agtgcaatga | ctgcaaccag | 780 |
| aaacagaagc | atgactcgtt | tagccactcc | agatctagga | ttaatgccta | taaggcctg | 840 |
| gcaagtccgg | cttacctgtc | attgtctagt | gaagatccag | tcatgacggc | tttagaactt | 900 |
| agcaatgaac | tggcagttct | ggccaatatt | gagaaagagt | tcaagaatga | ctacaaaaaa | 960 |
| ctgtcaatgc | agtgcaaaga | ctttgttgtt | ggactccttg | atctgtgcag | aaacactgaa | 1020 |
| gaagtcgagg | ccattctgaa | tggggatgtt | gaaacgctcc | agagtggtga | tcacggtcgc | 1080 |
| ccaaatctca | gccgtttaaa | acttgccatt | aaatatgaag | taaaaaatt | tgtagctcat | 1140 |
| ccaaactgcc | aacagcaact | tctctccatt | tggtatgaga | tctttctgg | tttacgacag | 1200 |
| cagacaatgg | cggtcaagtt | ccttgtggtc | cttgctgttg | ccattggact | gcccttcctg | 1260 |
| gctctcattt | actggtttgc | tccatgcagc | aagatgggga | agataatgcg | tggaccattc | 1320 |
| atgaagtttg | tagcacacgc | agcctccttc | accattttc | tgggactgct | agtcatgaat | 1380 |
| gcagctgaca | gatttgaagg | cacaaaactc | cttcctaatg | aaaccagcac | agataatgca | 1440 |
| aaacagctgt | tcaggatgaa | aacatcctgc | ttctcatgga | tggagatgct | cattatatcc | 1500 |
| tgggtaatag | gcatgatatg | ggctgaatgt | aaagaaatct | ggactcaggg | ccccaaggaa | 1560 |
| tatttgtttg | agttgtggaa | catgcttgat | tttggtatgt | tagcaatttt | cgcagcatca | 1620 |
| ttcattgcga | gattcatggc | attttggcat | gcttccaaag | cccagagcat | cattgacgca | 1680 |
| aacgatactt | tgaaggactt | gacgaaagta | acattgggag | acaatgtgaa | atactacaat | 1740 |
| ttggccagga | taaagtggga | cccctctgat | cctcaaataa | tatctgaagg | tctttatgca | 1800 |
| attgctgtag | ttttaagttt | ctctaggata | gcttatattt | taccagcaaa | tgaaagcttt | 1860 |
| ggacctctgc | agatatcact | tggaagaaca | gtcaaagaca | tcttcaagtt | catggtcata | 1920 |

```
ttcattatgg tgtttgtggc ctttatgatt ggaatgttca atctctactc ctactacatt    1980
ggtgcaaaac aaaatgaagc cttcacaaca gttgaagaga gttttaagac agcggccgcg    2040
gctatatttg gactttctga agtgaaatca gtggtcatca actataacca caaattcatt    2100
gaaaacattg gttacgttct ttatggagtc tataatgtta cgatggtcat tgttttgcta    2160
aatatgttaa ttgccatgat caacagttca ttccaggaaa ttgaggatga cgctgatgtg    2220
gagtggaaat ttgcaagggc caaactctgg ttttcctact tgaggaggg cagaacactt    2280 cctgtaccct tcaatctggt gccgagtcca aagtccctgt tttatctctt actgaagctt    2340
aaaaaatgga tttctgagct gttccagggc cataaaaaag gtttccagga agatgcagag    2400
atgaacaaga taaatgaaga aagaaacttg gaattttag gaagtcatga agacctttca    2460
aaattatcac ttgacaaaaa acaggttggg cacaataaac aaccaagtat aaggagctca    2520
gaagatttcc atctaaatag tttcaataat cctccaagac aatatcagaa ataatgaaa    2580 aggctcatta aaagatatgt actgcaggcc cagatagata aggagagtga tgaagtgaac    2640 gaagggaac tgaaggaaat taagcaggac atctcaagtc tccgctatga actccttgaa    2700
gaaaaatctc agaatacaga agacctagca gaacttatta gagaacttgg agagaaatta    2760
tccatggaac caaatcaaga ggaaaccaat agataa                              2796
```

<210> SEQ ID NO 9
<211> LENGTH: 862
<212> TYPE: PRT
<213> ORGANISM: Homo sapiens

<400> SEQUENCE: 9

```
Met Leu Arg Asn Ser Thr Phe Lys Asn Met Gln Arg Arg His Thr Thr
  1               5                  10                  15

Leu Arg Glu Lys Gly Arg Arg Gln Ala Ile Arg Gly Pro Ala Tyr Met
             20                  25                  30

Phe Asn Glu Lys Gly Thr Ser Leu Thr Pro Glu Glu Arg Phe Leu
         35                  40                  45

Asp Ser Ala Glu Tyr Gly Asn Ile Pro Val Val Arg Lys Met Leu Glu
     50                  55                  60

Glu Ser Lys Thr Leu Asn Phe Asn Cys Val Asp Tyr Met Gly Gln Asn
 65                  70                  75                  80

Ala Leu Gln Leu Ala Val Gly Asn Glu His Leu Glu Val Thr Glu Leu
                 85                  90                  95

Leu Leu Lys Lys Glu Asn Leu Ala Arg Val Gly Asp Ala Leu Leu Leu
            100                 105                 110

Ala Ile Ser Lys Gly Tyr Val Arg Ile Val Glu Ala Ile Leu Asn His
        115                 120                 125

Pro Ala Phe Ala Gln Gly Gln Arg Leu Thr Leu Ser Pro Leu Glu Gln
    130                 135                 140

Glu Leu Arg Asp Asp Phe Tyr Ala Tyr Asp Glu Asp Gly Thr Arg
145                 150                 155                 160

Phe Ser His Asp Ile Thr Pro Ile Ile Leu Ala Ala His Cys Gln Glu
                165                 170                 175

Tyr Glu Ile Val His Ile Leu Leu Leu Lys Gly Ala Arg Ile Glu Arg
            180                 185                 190

Pro His Asp Tyr Phe Cys Lys Cys Asn Glu Cys Thr Glu Lys Gln Arg
        195                 200                 205

Lys Asp Ser Phe Ser His Ser Arg Ser Arg Met Asn Ala Tyr Lys Gly
    210                 215                 220
```

```
Leu Ala Ser Ala Ala Tyr Leu Ser Leu Ser Ser Glu Asp Pro Val Leu
225                 230                 235                 240

Thr Ala Leu Glu Leu Ser Asn Glu Leu Ala Arg Leu Ala Asn Ile Glu
            245                 250                 255

Thr Glu Phe Lys Asn Asp Tyr Arg Lys Leu Ser Met Gln Cys Lys Asp
        260                 265                 270

Phe Val Val Gly Val Leu Asp Leu Cys Arg Asp Thr Glu Glu Val Glu
    275                 280                 285

Ala Ile Leu Asn Gly Asp Val Asn Phe Gln Val Trp Ser Asp His His
290                 295                 300

Arg Pro Ser Leu Ser Arg Ile Lys Leu Ala Ile Lys Tyr Glu Val Lys
305                 310                 315                 320

Lys Phe Val Ala His Pro Asn Cys Gln Gln Gln Leu Leu Thr Met Trp
                325                 330                 335

Tyr Glu Asn Leu Ser Gly Leu Arg Gln Gln Ser Ile Ala Val Lys Phe
            340                 345                 350

Leu Ala Val Phe Gly Val Ser Ile Gly Leu Pro Phe Leu Ala Ile Ala
        355                 360                 365

Tyr Trp Ile Ala Pro Cys Ser Lys Leu Gly Arg Thr Leu Arg Ser Pro
    370                 375                 380

Phe Met Lys Phe Val Ala His Ala Val Ser Phe Thr Ile Phe Leu Gly
385                 390                 395                 400

Leu Leu Val Val Asn Ala Ser Asp Arg Phe Glu Gly Val Lys Thr Leu
                405                 410                 415

Pro Asn Glu Thr Phe Thr Asp Tyr Pro Lys Gln Ile Phe Arg Val Lys
            420                 425                 430

Thr Thr Gln Phe Ser Trp Thr Glu Met Leu Ile Met Lys Trp Val Leu
        435                 440                 445

Gly Met Ile Trp Ser Glu Cys Lys Glu Ile Trp Glu Glu Gly Pro Arg
    450                 455                 460

Glu Tyr Val Leu His Leu Trp Asn Leu Leu Asp Phe Gly Met Leu Ser
465                 470                 475                 480

Ile Phe Val Ala Ser Phe Thr Ala Arg Phe Met Ala Phe Leu Lys Ala
                485                 490                 495

Thr Glu Ala Gln Leu Tyr Val Asp Gln His Val Gln Asp Asp Thr Leu
            500                 505                 510

His Asn Val Ser Leu Pro Pro Glu Val Ala Tyr Phe Thr Tyr Ala Arg
        515                 520                 525

Asp Lys Trp Trp Pro Ser Asp Pro Gln Ile Ile Ser Glu Gly Leu Tyr
    530                 535                 540

Ala Ile Ala Val Val Leu Ser Phe Ser Arg Ile Ala Tyr Ile Leu Pro
545                 550                 555                 560

Ala Asn Glu Ser Phe Gly Pro Leu Gln Ile Ser Leu Gly Arg Thr Val
                565                 570                 575

Lys Asp Ile Phe Lys Phe Met Val Ile Phe Ile Met Val Phe Val Ala
            580                 585                 590

Phe Met Ile Gly Met Phe Asn Leu Tyr Ser Tyr Arg Gly Ala Lys
        595                 600                 605

Tyr Asn Pro Ala Phe Thr Thr Val Glu Glu Ser Phe Lys Thr Leu Phe
    610                 615                 620

Trp Ser Ile Phe Gly Leu Ser Glu Val Ile Ser Val Val Leu Lys Tyr
625                 630                 635                 640

Asp His Lys Phe Ile Glu Asn Ile Gly Tyr Val Leu Tyr Gly Val Tyr
                645                 650                 655
```

```
Asn Val Thr Met Val Val Leu Leu Asn Met Leu Ile Ala Met Ile
                660                 665                 670

Asn Asn Ser Tyr Gln Glu Ile Glu Glu Asp Ala Asp Val Glu Trp Lys
            675                 680                 685

Phe Ala Arg Ala Lys Leu Trp Leu Ser Tyr Phe Asp Glu Gly Arg Thr
        690                 695                 700

Leu Pro Ala Pro Phe Asn Leu Val Pro Ser Pro Lys Ser Phe Tyr Tyr
705                 710                 715                 720

Leu Ile Met Arg Ile Lys Met Cys Leu Ile Lys Leu Cys Lys Ser Lys
                725                 730                 735

Ala Lys Ser Cys Glu Asn Asp Leu Glu Met Gly Met Leu Asn Ser Lys
            740                 745                 750

Phe Lys Lys Thr Arg Tyr Gln Ala Gly Met Arg Asn Ser Glu Asn Leu
        755                 760                 765

Thr Ala Asn Asn Thr Leu Ser Lys Pro Thr Arg Tyr Gln Lys Ile Met
770                 775                 780

Lys Arg Leu Ile Lys Arg Tyr Val Leu Lys Ala Gln Val Asp Arg Glu
                785                 790                 795                 800

Asn Asp Glu Val Asn Glu Gly Glu Leu Lys Glu Ile Lys Gln Asp Ile
            805                 810                 815

Ser Ser Leu Arg Tyr Glu Leu Leu Glu Glu Lys Ser Gln Ala Thr Gly
        820                 825                 830

Glu Leu Ala Asp Leu Ile Gln Gln Leu Ser Gly Lys Phe Gly Lys Asn
    835                 840                 845

Leu Asn Lys Asp His Leu Arg Val Asn Lys Gly Lys Asp Ile
850                 855                 860

<210> SEQ ID NO 10
<211> LENGTH: 2589
<212> TYPE: DNA
<213> ORGANISM: Homo sapiens

<400> SEQUENCE: 10
atgttgagga cagcacccct caaaaacatg cagcgccggc acacaacgct gagggagaag      60
ggccgtcgcc aggccatccg gggtcccgcc tacatgttca cgagaagggg caccagtctg     120
acgcccgagg aggagcgctt cctggactcg gctgagtatg caacatccc ggtggtccgg      180 aaaatgctgg aggagtccaa gacccttaac ttcaactgtg tggactacat ggggcagaac     240
gctctgcagc tggccgtggg caacgagcac ctagaggtca cggagctgct gctgaagaag     300
gagaacctgg cacgggtggg ggacgcgctg ctgctggcca tcagcaaggg ctatgtgcgc     360
atcgtggagc ccatcctcaa ccaccgcc ttcgcgcagg ccagcgcct gacgctcagc       420 ccgctggaac aggagctgcg cgacgacgac ttctatgcct acgacgagga cggcacgcgc     480
ttctcccacg acatcacgcc catcatcctg cggcgcact gccaggagta tgagatcgtg      540
cacatcctgc tgctcaaggg cgcccgcatc gagcggcccc acgactactt ctgcaagtgc     600
aatgagtgca ccgagaaaca gcggaaagac tccttcagcc actcgcgctc gcgcatgaac     660
gcctacaaag gactggcgag tgctgcctac ttgtccctgt ccagcgaaga ccctgtcctc     720
accgccctgg agctcagcaa cgagttagcc agactagcca acattgagac tgaatttaag     780
aacgattaca ggaagttatc tatgcaatgc aaggattttg tagtgggcgt gctggacctg     840
tgccgagaca cagaagaggt ggaagcaatt ttaaacggtg atgtgaactt ccaagtctgg     900
tccgaccacc accgtccaag tctgagccgg atcaaactcg ccattaaata tgaagtcaag     960
```

-continued

```
aagttcgttg ctcatcctaa ctgtcagcag caattgctta ccatgtggta tgaaaatctc    1020
tcaggcttac gtcaacagtc tatcgctgtg aaattcctgg ctgtctttgg agtctccata    1080
ggcctccctt ttctcgccat agcctattgg attgctccgt gcagcaagct aggacgaacc    1140
ctgaggagcc ctttcatgaa gtttgtagct catgcagttt cttttacaat cttcttggga    1200
ttattagttg tgaatgcatc tgaccgattt gaaggtgtta aaaccctgcc aaacgaaacc    1260
ttcacagact acccaaaaca aatcttcaga gtgaaaacca cacagttctc ctggacagaa    1320
atgctcatta tgaagtgggt cttaggaatg atttggtccg aatgcaagga atctgggag    1380 gaggggccac gggagtacgt gctgcacttg tggaacctgc tagatttcgg gatgctgtcc    1440
atcttcgtgg cctccttcac agcacgcttc atggccttcc tgaaggccac ggaggcacag    1500
ctgtacgtgg accagcacgt gcaggacgac acgctgcaca atgtctcgct tccgccggaa    1560
gtggcatact tcacctacgc cagggacaag tggtggcctt cagaccctca gatcatatcg    1620
gaagggctct acgcgatagc cgtcgtgctg agcttctctc gcattgcata cattctgcca    1680
gccaacgaga gttttgggcc cctgcagatc tcgctaggga gaactgtgaa agatatcttc    1740
aagttcatgg tcattttcat catggtattt gtggccttca tgattgggat gttcaacctg    1800
tactcttact accgaggtgc caaatacaac ccagcgttta caacggttga agaaagtttt    1860
aaaactttgt tttggtccat attcggctta tctgaagtaa tctcagtggt gctgaaatac    1920
gaccacaaat tcatcgagaa cattggctac gttctctacg gcgtttataa cgtcaccatg    1980
gtggtagtgt tgctcaacat gctaatagcc atgataaaca actcctatca ggaaattgag    2040
gaggatgcag atgtggaatg gaagttcgcc cgagcaaaac tctggctgtc ttactttgat    2100
gaaggaagaa ctctacctgc tcctttttaat ctagtgccaa gtcctaaatc attttattat    2160
ctcataatga gaatcaagat gtgcctcata aaactctgca atctaaggc caaaagctgt    2220 gaaaatgacc ttgaaatggg catgctgaat tccaaattca agaagactcg ctaccaggct    2280
ggcatgagga attctgaaaa tctgacagca ataacacttt tgagcaagcc caccagatac    2340
cagaaaatca tgaaacggct cataaaaaga tacgtcctga agcccaggt ggacagagaa    2400 aatgacgaag tcaatgaagg cgagctgaag gaaatcaagc aagatatctc cagcctgcgc    2460
tatgagcttc ttgaggaaaa atctcaagct actggtgagc tggcagacct gattcaacaa    2520
ctcagcgaga gtttggaaa gaacttaaac aaagaccacc tgagggtgaa caagggcaaa    2580
gacatttag                                                            2589
```

<210> SEQ ID NO 11
<211> LENGTH: 862
<212> TYPE: PRT
<213> ORGANISM: Artificial Sequence
<220> FEATURE:
<223> OTHER INFORMATION: Description of Artificial Sequence: mutant

<400> SEQUENCE: 11

```
Met Leu Arg Asn Ser Thr Phe Lys Asn Met Gln Arg His Thr Thr
1               5                   10                  15

Leu Arg Glu Lys Gly Arg Arg Gln Ala Ile Arg Gly Pro Ala Tyr Met
                20                  25                  30

Phe Asn Glu Lys Gly Thr Ser Leu Thr Pro Glu Glu Arg Phe Leu
            35                  40                  45

Asp Ser Ala Glu Tyr Gly Asn Ile Pro Val Val Arg Lys Met Leu Glu
        50                  55                  60

Glu Ser Lys Thr Leu Asn Phe Asn Cys Val Asp Tyr Met Gly Gln Asn
65                  70                  75                  80
```

-continued

```
Ala Leu Gln Leu Ala Val Gly Asn Glu His Leu Glu Val Thr Glu Leu
                 85                  90                  95
Leu Leu Lys Lys Glu Asn Leu Ala Arg Val Gly Asp Ala Leu Leu Leu
            100                 105                 110
Ala Ile Ser Lys Gly Tyr Val Arg Ile Val Glu Ala Ile Leu Asn His
        115                 120                 125
Pro Ala Phe Ala Gln Gly Gln Arg Leu Thr Leu Ser Pro Leu Glu Gln
130                 135                 140
Glu Leu Arg Asp Asp Asp Phe Tyr Ala Tyr Asp Glu Asp Gly Thr Arg
145                 150                 155                 160
Phe Ser His Asp Ile Thr Pro Ile Ile Leu Ala Ala His Cys Gln Glu
                165                 170                 175
Tyr Glu Ile Val His Ile Leu Leu Leu Lys Gly Ala Arg Ile Glu Arg
            180                 185                 190
Pro His Asp Tyr Phe Cys Lys Cys Asn Glu Cys Thr Glu Lys Gln Arg
        195                 200                 205
Lys Asp Ser Phe Ser His Ser Arg Ser Arg Met Asn Ala Tyr Lys Gly
210                 215                 220
Leu Ala Ser Ala Ala Tyr Leu Ser Leu Ser Ser Glu Asp Pro Val Leu
225                 230                 235                 240
Thr Ala Leu Glu Leu Ser Asn Glu Leu Ala Arg Leu Ala Asn Ile Glu
                245                 250                 255
Thr Glu Phe Lys Asn Asp Tyr Arg Lys Leu Ser Met Gln Cys Lys Asp
            260                 265                 270
Phe Val Val Gly Val Leu Asp Leu Cys Arg Asp Thr Glu Glu Val Glu
        275                 280                 285
Ala Ile Leu Asn Gly Asp Val Asn Phe Gln Val Trp Ser Asp His His
290                 295                 300
Arg Pro Ser Leu Ser Arg Ile Lys Leu Ala Ile Lys Tyr Glu Val Lys
305                 310                 315                 320
Lys Phe Val Ala His Pro Asn Cys Gln Gln Gln Leu Leu Thr Met Trp
                325                 330                 335
Tyr Glu Asn Leu Ser Gly Leu Arg Gln Gln Ser Ile Ala Val Lys Phe
            340                 345                 350
Leu Ala Val Phe Gly Val Ser Ile Gly Leu Pro Phe Leu Ala Ile Ala
        355                 360                 365
Tyr Trp Ile Ala Pro Cys Ser Lys Leu Gly Arg Thr Leu Arg Ser Pro
370                 375                 380
Phe Met Lys Phe Val Ala His Ala Val Ser Phe Thr Ile Phe Leu Gly
385                 390                 395                 400
Leu Leu Val Val Asn Ala Ser Asp Arg Phe Glu Gly Val Lys Thr Leu
                405                 410                 415
Pro Asn Glu Thr Phe Thr Asp Tyr Pro Lys Gln Ile Phe Arg Val Lys
            420                 425                 430
Thr Thr Gln Phe Ser Trp Thr Glu Met Leu Ile Met Lys Trp Val Leu
        435                 440                 445
Gly Met Ile Trp Ser Glu Cys Lys Glu Ile Trp Glu Glu Gly Pro Arg
450                 455                 460
Glu Tyr Val Leu His Leu Trp Asn Leu Leu Asp Phe Gly Met Leu Ser
465                 470                 475                 480
Ile Phe Val Ala Ser Phe Thr Ala Arg Phe Met Ala Phe Leu Lys Ala
                485                 490                 495
Thr Glu Ala Gln Leu Tyr Val Asp Gln His Val Gln Asp Asp Thr Leu
```

```
                    500                 505                 510
His Asn Val Ser Leu Pro Pro Glu Val Ala Tyr Phe Thr Tyr Ala Arg
            515                 520                 525

Asp Lys Trp Pro Ser Asp Pro Gln Ile Ile Ser Glu Gly Leu Tyr
        530                 535                 540

Ala Ile Ala Val Val Leu Ser Phe Ser Arg Ile Ala Tyr Ile Leu Pro
545                 550                 555                 560

Ala Asn Glu Ser Phe Gly Pro Leu Gln Ile Ser Leu Gly Arg Thr Val
            565                 570                 575

Lys Asp Ile Phe Lys Phe Met Val Ile Phe Ile Met Val Phe Val Ala
        580                 585                 590

Phe Met Ile Gly Met Phe Asn Leu Tyr Ser Tyr Tyr Arg Gly Ala Lys
            595                 600                 605

Tyr Asn Pro Ala Phe Thr Thr Val Glu Glu Ser Phe Lys Thr Ala Ala
        610                 615                 620

Ala Ser Ile Phe Gly Leu Ser Glu Val Ile Ser Val Val Leu Lys Tyr
625                 630                 635                 640

Asp His Lys Phe Ile Glu Asn Ile Gly Tyr Val Leu Tyr Gly Val Tyr
            645                 650                 655

Asn Val Thr Met Val Val Val Leu Leu Asn Met Leu Ile Ala Met Ile
        660                 665                 670

Asn Asn Ser Tyr Gln Glu Ile Glu Glu Asp Ala Asp Val Glu Trp Lys
            675                 680                 685

Phe Ala Arg Ala Lys Leu Trp Leu Ser Tyr Phe Asp Glu Gly Arg Thr
690                 695                 700

Leu Pro Ala Pro Phe Asn Leu Val Pro Ser Pro Lys Ser Phe Tyr Tyr
705                 710                 715                 720

Leu Ile Met Arg Ile Lys Met Cys Leu Ile Lys Leu Cys Lys Ser Lys
            725                 730                 735

Ala Lys Ser Cys Glu Asn Asp Leu Glu Met Gly Met Leu Asn Ser Lys
        740                 745                 750

Phe Lys Lys Thr Arg Tyr Gln Ala Gly Met Arg Asn Ser Glu Asn Leu
            755                 760                 765

Thr Ala Asn Asn Thr Leu Ser Lys Pro Thr Arg Tyr Gln Lys Ile Met
        770                 775                 780

Lys Arg Leu Ile Lys Arg Tyr Val Leu Lys Ala Gln Val Asp Arg Glu
785                 790                 795                 800

Asn Asp Glu Val Asn Glu Gly Glu Leu Lys Glu Ile Lys Gln Asp Ile
            805                 810                 815

Ser Ser Leu Arg Tyr Glu Leu Leu Glu Glu Lys Ser Gln Ala Thr Gly
        820                 825                 830

Glu Leu Ala Asp Leu Ile Gln Gln Leu Ser Glu Lys Phe Gly Lys Asn
            835                 840                 845

Leu Asn Lys Asp His Leu Arg Val Asn Lys Gly Lys Asp Ile
        850                 855                 860

<210> SEQ ID NO 12
<211> LENGTH: 2589
<212> TYPE: DNA
<213> ORGANISM: Artificial Sequence
<220> FEATURE:
<223> OTHER INFORMATION: Description of Artificial Sequence: mutant

<400> SEQUENCE: 12
atgttgagga acagcacctt caaaaacatg cagcgccggc acacaacgct gagggagaag     60
```

```
ggccgtcgcc aggccatccg gggtcccgcc tacatgttca acgagaaggg caccagtctg    120
acgcccgagg aggagcgctt cctggactcg gctgagtatg caacatccc ggtggtccgg     180 aaaatgctgg aggagtccaa gacccttaac ttcaactgtg tggactacat ggggcagaac    240
gctctgcagc tggccgtggg caacgagcac ctagaggtca cggagctgct gctgaagaag    300
gagaacctgg cacgggtggg ggacgcgctg ctgctggcca tcagcaaggg ctatgtgcgc    360
atcgtggagc ccatcctcaa ccacccggcc ttcgcgcagg gccagcgcct gacgctcagc    420
ccgctggaac aggagctgcg cgacgacgac ttctatgcct acgacgagga cggcacgcgc    480
ttctcccacg acatcacgcc catcatcctg gcggcgcact gccaggagta tgagatcgtg    540
cacatcctgc tgctcaaggg cgcccgcatc gagcggcccc acgactactt ctgcaagtgc    600
aatgagtgca ccgagaaaca gcggaaagac tccttcagcc actcgcgctc gcgcatgaac    660
gcctacaaag gactggcgag tgctgcctac ttgtccctgt ccagcgaaga ccctgtcctc    720
accgccctgg agctcagcaa cgagttagcc agactagcca acattgagac tgaatttaag    780
aacgattaca ggaagttatc tatgcaatgc aaggattttg tagtgggcgt gctggacctg    840
tgccgagaca cagaagaggt ggaagcaatt ttaaacggtg atgtgaactt ccaagtctgg    900
tccgaccacc accgtccaag tctgagccgg atcaaactcg ccattaaata tgaagtcaag    960
aagttcgttg ctcatcctaa ctgtcagcag caattgctta ccatgtggta tgaaaatctc   1020
tcaggcttac gtcaacagtc tatcgctgtg aaattcctgg ctgtctttgg agtctccata   1080
ggcctccctt ttctcgccat agcctattgg attgctccgt gcagcaagct aggacgaacc   1140
ctgaggagcc ctttcatgaa gtttgtagct catgcagttt cttttacaat cttcttggga   1200
ttattagttg tgaatgcatc tgaccgattt gaaggtgtta aaaccctgcc aaacgaaacc   1260
ttcacagact acccaaaaca aatcttcaga gtgaaaacca cacagttctc ctggacagaa   1320
atgctcatta tgaagtgggt cttaggaatg atttggtccg aatgcaagga aatctgggag   1380
gaggggccac gggagtacgt gctgcacttg tggaacctgc tagatttcgg gatgctgtcc   1440
atcttcgtgg cctccttcac agcacgcttc atggccttcc tgaaggccac ggaggcacag   1500
ctgtacgtgg accagcacgt gcaggacgac acgctgcaca atgtctcgct tccgccggaa   1560
gtggcatact tcacctacgc cagggacaag tggtggcctt cagaccctca gatcatatcg   1620
gaagggctct acgcgatagc cgtcgtgctg agcttctctc gcattgcata cattctgcca   1680
gccaacgaga gttttgggcc cctgcagatc tcgctaggga gaactgtgaa agatatcttc   1740
aagttcatgg tcattttcat catggtattt gtggccttca tgattgggat gttcaacctg   1800
tactcttact accgaggtgc caaatacaac ccagcgttta caacggttga agaaagtttt   1860
aaaactgcgg ctgcgtccat attcggctta tctgaagtaa tctcagtggt gctgaaatac   1920
gaccacaaat tcatcgagaa cattggctac gttctctacg cgtttataaa cgtcaccatg   1980
gtggtagtgt tgctcaacat gctaatagcc atgataaaca actcctatca ggaaattgag   2040
gaggatgcag atgtggaatg gaagttcgcc cgagcaaaac tctggctgtc ttactttgat   2100
gaaggaagaa ctctacctgc tccttttaat ctagtgccaa gtcctaaatc atttttattat   2160 ctcataatga gaatcaagat gtgcctcata aaactctgca aatctaaggc caaaagctgt   2220
gaaaatgacc ttgaaatggg catgctgaat tccaaattca gaagactcg ctaccaggct    2280 ggcatgagga attctgaaaa tctgacagca aataacactt tgagcaagcc caccagatac   2340
```

-continued

```
cagaaaatca tgaaacggct cataaaaaga tacgtcctga aagcccaggt ggacagagaa    2400
aatgacgaag tcaatgaagg cgagctgaag gaaatcaagc aagatatctc cagcctgcgc    2460
tatgagcttc ttgaggaaaa atctcaagct actggtgagc tggcagacct gattcaacaa    2520
ctcagcgaga agtttggaaa gaacttaaac aaagaccacc tgagggtgaa caagggcaaa    2580
gacatttag                                                           2589
```